United States Patent [19]

Janssens et al.

[11] Patent Number: 5,086,056
[45] Date of Patent: Feb. 4, 1992

[54] 2-(HETEROCYCLYLALKYL)IMIDAZOPYRIDINES

[75] Inventors: Frans E. Janssens, Bonheiden; François M. Sommen, Wortel; Joseph L. G. Torremans, Beerse; Gaston S. M. Diels, Ravels, all of Belgium

[73] Assignee: Janssen Pharmaceutica N.V., Belgium

[21] Appl. No.: 652,828

[22] Filed: Feb. 8, 1991

Related U.S. Application Data

[60] Division of Ser. No. 561,833, Aug. 2, 1990, Pat. No. 5,011,842, which is a continuation of Ser. No. 211,652, Jun. 27, 1988, Pat. No. 4,946,843.

[30] Foreign Application Priority Data

Jul. 10, 1987 [GB] United Kingdom ............... 8716313

[51] Int. Cl.$^5$ ............... A61K 31/495; A61K 31/505; A61K 31/52; C07D 473/00; C07D 403/14
[52] U.S. Cl. ............... 514/253; 514/218; 514/261; 514/266; 540/575; 544/264; 544/277; 544/295; 544/296; 544/362
[58] Field of Search ............... 544/264, 277; 514/253, 514/261, 266

[56] References Cited

U.S. PATENT DOCUMENTS

| 4,548,820 | 10/1985 | Regnier et al. | 514/255 |
| 4,599,338 | 7/1986 | Ragnier et al. | 514/265 |
| 4,603,130 | 7/1986 | Iemura et al. | 514/218 |
| 4,603,204 | 7/1986 | Thiele et al. | 544/267 |
| 4,695,575 | 9/1987 | Janssens et al. | 514/322 |

FOREIGN PATENT DOCUMENTS 667333 1/1966 Belgium .
123962 7/1984 European Pat. Off. .

OTHER PUBLICATIONS

R. Iemura et al., J. Heterocyclic Chem. 24,31–37 (1987).
G. Cleve et al., Liebig's Ann. Chem. 747, 158–171 (1971).
T. Kovac, et al., J. Heterocyclic Chem. 20, 1339 (1983).

Primary Examiner—Cecilia Shen
Attorney, Agent, or Firm—Charles J. Metz

[57] ABSTRACT 2-(Heterocyclylalkyl)imidazopyridines having antihistaminic properties, compositions containing these compounds as active ingredient and novel 2-(Heterocyclylalkyl)imidazopyridines.

24 Claims, No Drawings

2-(HETEROCYCLYLALKYL)IMIDAZOPYRI-DINES

CROSS-REFERENCE TO RELATED APPLICATIONS:

This application is a division of application Ser. No. 561,833 filed on Aug. 2, 1990, now U.S. Pat. No. 5,011,842, which was a division of application Ser. No. 211,652, filed on June 27, 1988, now U.S. Pat. No. 4,946,843.

BACKGROUND OF THE INVENTION

In published European Patent Application No. 123,962 and in Journal of Heterocyclic Chemistry, 24, 31-37 there are described a number of 2-heterocyclylmethyl-1-alkoxyethylbenzimidazole derivatives as compounds possessing antihistaminic activity.

A number of 2-heterocyclylmethyl-1-benzylimidazo[4,5-b]- and imidazo[4,5-c]pyridines are described in Liebigs Ann. Chem. 747, 158-171 (1971) as compounds possessing inflammatory reducing properties.

In J. Heterocyclic Chem. 20, 1339 (1983) there is described the preparation of the compound 3-(methylphenyl)-2-[(4-methyl-1-piperazinyl)methyl]-3H-imidazo[4,5-b]pyridine.

Belgium Patent No. 667,333 on the other hand teaches 2-(piperazinylalkyl)-1-substituted benzimidazoles possessing antihypertensive and anti-allergic properties.

DESCRIPTION OF THE INVENTION

The present invention is concerned with a method of treating warm-blooded animals suffering from allergic diseases, said method comprise the systemic administration to said warm-blooded animals of an effective anti-allergic amount of a compound having the formula

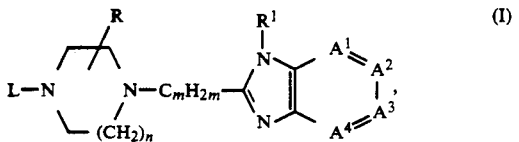

the pharmaceutically acceptable acid addition salts and the stereochemically isomeric forms thereof, wherein $-A^1=A^2-A^3=A^4-$ is a bivalent radical having the formula $-N=CH-CH=CH-$     (a-1), $-CH=N-CH=CH-$     (a-2), $-CH=CH-N=CH-$     (a-3), $-CH=CH-CH=N-$     (a-4), $-N=CH-N=CH-$     (a-5), or $-CH=N-CH=N-$     (a-6), wherein one or two hydrogen atoms in said radicals (a-1)–(a-6) may, each independently from each other, be replaced by halo, $C_{1-6}$alkyl, $C_{1-6}$alkyloxy, trifluoromethyl or hydroxy;

$R^1$ is hydrogen, $C_{1-10}$alkyl, $C_{3-6}$cycloalkyl, $Ar^1$, $C_{1-6}$alkyl substituted with one or two $Ar^1$ radicals, or a radical of formula $-Alk-G-R^2$; wherein $R^2$ is hydrogen; $C_{2-6}$alkenyl optionally substituted with $Ar^2$; $C_{3-6}$alkynyl; $Ar^1$ or $C_{1-6}$alkyl optionally substituted with $Ar^1$, hydroxy, $C_{1-6}$alkyloxy, carboxyl, $C_{1-6}$alkyloxycarbonyl, $Ar^2$-oxycarbonyl or $Ar^2$-$C_{1-6}$alkyloxycarbonyl; and G is O, S or $NR^3$; said $R^3$ being hydrogen, $C_{1-6}$alkyl, $C_{1-6}$alkylcarbonyl, $C_{1-6}$alkyloxycarbonyl or $Ar^2$—$C_{1-6}$alkyl;

R is hydrogen or $C_{1-6}$alkyl;

m is 1 to 4;

n is 1 or 2;

L is hydrogen, $C_{1-6}$alkylcarbonyl, $C_{1-6}$alkylsulfonyl, $C_{1-6}$alkyloxycarbonyl, $Ar^2$—$C_{1-6}$alkyloxycarbonyl, $Ar^2$-carbonyl, $Ar^2$-sulfonyl, $C_{3-6}$cycloalkyl, $C_{2-6}$alkenyl optionally substituted with $Ar^2$, $C_{1-12}$alkyl, a radical of formula $-Alk-R^4$     (b-1)

$-Alk-Y-R^5$     (b-2)

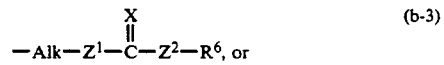     (b-3)

$-CH_2-CHOH-CH_2-O-R^7$     (b-4);

wherein $R^4$ is $Ar^2$, Het, cyano, isocyanato, isothiocyanato, $Ar^2$-sulfonyl or halo;

$R^5$ is hydrogen, $Ar^2$, Het or $C_{1-6}$alkyl optionally substituted with halo, $Ar^2$ or Het;

$R^6$ is hydrogen, $Ar^2$, Het or $C_{1-6}$alkyl optionally substituted with halo, Het or $Ar^2$;

$R^7$ is $Ar^2$ or naphthalenyl;

Y is O, S, $NR^8$; said $R^8$ being hydrogen, $C_{1-6}$alkyl, $C_{1-6}$alkylcarbonyl or $Ar^1$-carbonyl;

$Z^1$ and $Z^2$ each independently are O, S, $NR^9$ or a direct bond;

said $R^9$ being hydrogen or $C_{1-6}$alkyl;

X is O, S or $NR^{10}$; said $R^{10}$ being hydrogen, $C_{1-6}$alkyl or cyano;

and each Alk independently being $C_{1-6}$alkanediyl;

Het is a five- or six-membered heterocyclic ring containing 1, 2, 3 or 4 heteroatoms, said heteroatoms being selected from the group consisting of oxygen, sulfur and nitrogen, provided that no more than two oxygens or sulfurs are present, said five or six-membered ring being optionally condensed with a five- or six-membered carbocyclic or heterocyclic ring also containing 1, 2, 3 or 4 heteroatoms, the latter heteroatoms being selected from the group consisting of oxygen, sulfur and nitrogen, provided that no more than 2 oxygens or sulfurs are present, and when said Het is a bicyclic ring system it may optionally be substituted with up to 6 substituents, and when said Het is a monocyclic ring system it may optionally be substituted with up to 4 substituents, said substituents of Het being selected from the group consisting of a bivalent radical of formula =X; halo; isocyanato; isothiocyanato; nitro; cyano; trifluoromethyl; a radical of formula —A; a radical of formula —Y—A; or a radical of formula $-Z^1-C(=X)-Z^2-A$; wherein said =X independently has the same meaning of the previously defined X and A is hydrogen, Ar$^2$ or C$_{1-6}$alkyl being optionally substituted with Ar$^2$, C$_{1-6}$alkyloxy, Ar$^2$—O, hydroxy, or C$_{1-6}$alkyloxycarbonyl; and Y, Z$^1$ and Z$^2$ independently have the same meaning of the previously defined Y, Z$^1$ and Z$^2$; provided that (i) when in the radical —Y—A, A is hydrogen, then Y is other than a direct bond, or (ii) when in the radical —Z$^1$—C(=X)—Z$^2$—A, A is hydrogen and Z$^1$ is NR$^9$, O or S, then Z$^2$ is other than O or S; preferably the sum of heteroatoms in the above defined Het is less than 6;

Ar$^1$ is phenyl, being optionally substituted with 1, 2 or 3 substituents each independently selected from halo, hydroxy, nitro, cyano, trifluoromethyl, C$_{1-6}$alkyl, C$_{1-6}$alkyloxy, C$_{1-6}$alkylthio, mercapto, amino, mono- and di(C$_{1-6}$alkyl)amino, carboxyl, C$_{1-6}$alkyloxycarbonyl and C$_{1-6}$alkylcarbonyl; thienyl; halothienyl; furanyl; C$_{1-6}$alkyl substituted furanyl; pyridinyl; pyrimidinyl; pyrazinyl; thiazolyl or imidazolyl optionally substituted with C$_{1-6}$alkyl; and Ar$^2$ is phenyl being optionally substituted with 1, 2 or 3 substituents each independently selected from halo, hydroxy, nitro, cyano, trifluoromethyl, C$_{1-6}$alkyl, C$_{1-6}$alkyloxy, C$_{1-6}$alkylthio, mercapto, amino, mono- and di(C$_{1-6}$alkyl)amino, carboxyl, C$_{1-6}$alkyloxycarbonyl and C$_{1-6}$alkylcarbonyl.

An additional feature of the present invention comprises the fact that most of the compounds of formula (I) are novel and have especially been developed to be used as active substances in the method of the present invention. These novel compounds are the compounds of formula (I) as defined hereinabove, with the proviso that when L is C$_{1-2}$alkyl, R$^1$ is other than hydrogen, 2-methylphenyl, benzyl, 4-chlorobenzyl or 4-methoxybenzyl.

As used in the foregoing definitions the term "halo" is generic to fluoro, chloro, bromo and iodo; the term "C$_{1-6}$alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "C$_{1-12}$alkyl" is meant to include C$_{1-6}$alkyl radicals, as defined hereinabove, and the higher homologs thereof having from 7 to 12 carbon atoms; the term "C$_{3-6}$cycloalkyl" is generic to cyclopropyl, cyclobutyl, cyclopentyl and cyclohexyl; the term "C$_{2-6}$alkenyl" defines straight and branch chained hydrocarbon radicals containing one double bond and having from 2 to 6 carbon atoms such as, for example, ethenyl, 2-propenyl, 3-butenyl, 2-butenyl, 2-pentenyl, 3-pentenyl, 3-methyl-2-butenyl and the like; "C$_{3-6}$alkynyl" defines straight and branch chained hydrocarbon radicals containing one triple bond and having from 3 to 6 carbon atoms such as, for example, propargyl, 2-butynyl, 3-butynyl, 2-pentynyl, 3-pentynyl or 4-pentynyl; and when a C$_{3-6}$alkenyl or C$_{3-6}$alkynyl is substituted on a heteroatom, then the carbon atom of said C$_{3-6}$alkenyl or C$_{3-6}$alkynyl connected to said heteroatom preferably is saturated. It is clear that the C$_m$H$_{2m}$ moiety comprises as well straight as branch chained bivalent saturated hydrocarbon radicals.

The said acid addition salts as mentioned hereinabove are meant to comprise the therapeutically active non-toxic acid addition salt forms which the compounds of formula (I) are able to form. The latter can conveniently be obtained by treating the base form wich appropriate acids such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The compounds of formula (I) containing acidic protons may also be converted to their therapeutically active non-toxic metal or amine substitution salt forms by treatment with appropriate organic or inorganic bases.

The term acid addition salt also comprises the hydrates and solvent addition forms which the compounds of formula (I) are able to form. Examples of such forms are e.g. hydrates, alcoholates and the like.

From formula (I) it is evident that the compounds of this invention may have several asymmetric carbon atoms in their structure.

Pure isomeric forms of the compounds of formula (I) can be separated from the mixture by conventional separation methods. Preferably, if a specific stereoisomer is desired, said compound will be synthesized by stereoselective methods of preparation. These methods will advantageously employ enantiomerically pure starting materials.

It is evident that in the compounds of formula (I) wherein R$^4$, R$^5$ or R$^6$ is Het, said Het may be unsaturated or partly or completely saturated. The compounds of formula (I) wherein Het is a heterocycle which is substituted with a hydroxy, mercapto or amino radical may contain in their structure a keto-enol tautomeric system or a vinylogous system thereof, and consequently the compounds may be present in their keto forms as well as their enol form.

In particularly Het is (i) an optionally substituted five- or six-membered heterocyclic ring containing 1, 2, 3 or 4 heteroatoms selected from the group consisting of oxygen, sulfur and nitrogen, provided that no more than two oxygens or sulfurs are present; or Het is (ii) an optionally substituted five- or six-membered heterocyclic ring containing 1 or 2 heteroatoms selected from the group consisting of oxygen, sulfur and nitrogen, being fused with an optionally substituted five- or six-membered ring through two ring carbon atoms or one ring carbon and one ring nitrogen atom, containing in the remainder of the fused ring only carbon atoms; or Het is (iii) an optionally substituted five- or six-membered heterocyclic ring containing 1 or 2 heteroatoms selected from the group consisting of oxygen, sulfur and nitrogen, being fused with an optionally substituted five- or six-membered heterocyclic ring through two ring carbon atoms or one ring carbon and one ring nitrogen atom, containing in the remainder of the fused ring 1 or 2 heteroatoms selected from the group consisting of oxygen, sulfur and nitrogen; wherein Het may optionally be substituted with up to 4 substituents when Het is a monocyclic ring system, and wherein Het may optionally be substituted with up to 5 substituents when Het is a bicyclic ring system, said substituents being the same as previously described.

In more detail Het is a member selected from the group consisting of pyridinyl which is optionally substituted with one or two substituents each independently selected from halo, amino, mono- and di(C$_{1-6}$alkyl- )amino, Ar$^2$—C$_{1-6}$alkylamino, nitro, cyano, aminocarbonyl, C$_{1-6}$alkyl, C$_{1-6}$alkyloxy, C$_{1-6}$alkylthio, C$_{1-6}$alkyloxycarbonyl, hydroxy, C$_{1-6}$alkylcarbonyloxy, Ar$^2$—C$_{1-6}$alkyl and carboxyl; pyridinyloxide optionally substituted with nitro; pyrimidinyl which is optionally substituted with one or two substituents each independently selected from the group consisting of halo, amino, C$_{1-6}$alkylamino, Ar$^2$—C$_{1-6}$alkylamino, hydroxy, C$_{1-6}$alkyl, C$_{1-6}$alkyloxy, C$_{1-6}$alkylthio and Ar$^2$—C$_{1-6}$alkyl; pyridazinyl which is optionally substituted with C$_{1-6}$alkyl or halo; pyrazinyl which is optionally substituted with halo, amino or C$_{1-6}$alkyl; thienyl which is optionally substituted with halo or C$_{1-6}$alkyl; furanyl which is optionally substituted with halo or C$_{1-6}$alkyl; pyrrolyl which is optionally substituted with C$_{1-6}$alkyl; thiazolyl which is optionally substituted with C$_{1-6}$alkyl, C$_{1-6}$alkyloxycarbonyl, Ar$^2$ or Ar$^2$—C$_{1-6}$alkyl; imidazolyl which is optionally substituted with one or two substituents each independently selected from C$_{1-6}$alkyl, Ar$^2$—C$_{1-6}$alkyl and nitro; tetrazolyl which is optionally substituted with C$_{1-6}$alkyl; 1,3,4-thiadiazolyl which is optionally substituted with C$_{1-6}$alkyl; 5,6-dihydro-4H-1,3-thiazin-2-yl which is optionally substituted with C$_{1-6}$alkyl; 4,5-dihydrothiazolyl which is optionally substituted with C$_{1-6}$alkyl; oxazolyl which is optionally substituted with C$_{1-6}$alkyl; 4,5-dihydro-5-oxo-1H-tetrazolyl which is optionally substituted with C$_{1-6}$alkyl; 1,4-dihydro-2,4-dioxo-3(2H)-pyrimidinyl being optionally substituted with C$_{1-6}$alkyl; 4,5-dihydro-4-oxopyrimidinyl optionally substituted with up to 3 substituents selected from C$_{1-6}$alkyl, amino, C$_{1-6}$alkylaminocarbonylamino, Ar$^2$-aminocarbonylamino, Ar$^2$—C$_{1-6}$alkyl-amino and C$_{1-6}$alkylamino; 2-oxo-3-oxazolidinyl; indolyl which is optionally substituted with hydroxy or C$_{1-6}$alkyl; quinolinyl which is optionally substituted with hydroxy or C$_{1-6}$alkyl; quinazolinyl which is optionally substituted with hydroxy or C$_{1-6}$alkyl; quinoxalinyl which is optionally substituted with C$_{1-6}$alkyl; phthalazinyl which is optionally substituted with halo; 1,3-dioxo-1H-isoindol-2(3H)-yl; 2,3-dihydro-3-oxo-4H-benzoxazinyl and 2,3-dihydro-1,4-benzodioxinyl, both being optionally substituted with C$_{1-6}$alkyl or halo; dioxanyl being optionally substituted with C$_{1-6}$alkyl; 2-oxo-2H-1-benzopyranyl and 4-oxo-4H-1-benzopyranyl both being optionally substituted with C$_{1-6}$alkyl; morfolinyl; thiomorfolinyl; piperidinyl; pyrolidinyl and a radical of formula

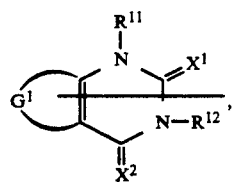 (c-1)

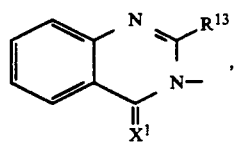 (c-2)

-continued

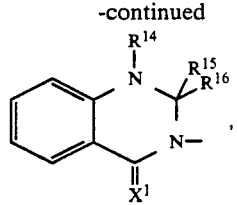 (c-3)

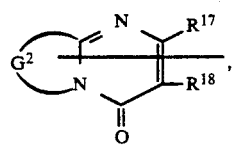 (c-4)

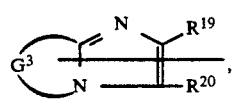 (c-5)

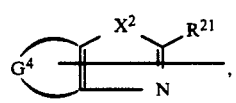 (c-6)

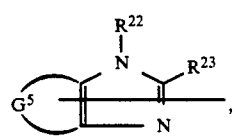 (c-7)

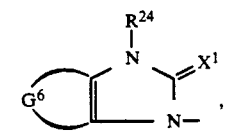 (c-8)

wherein

X$^1$ and X$^2$ are each independently O or S;

R$^{11}$, R$^{12}$, R$^{14}$, R$^{22}$ and R$^{24}$ are each independently hydrogen, C$_{1-6}$alkyl, Ar$^2$—C$_{1-6}$alkyl, C$_{1-6}$alkyloxyC$_{1-6}$alkyl, hydroxyC$_{1-6}$alkyl or C$_{1-6}$alkyloxycarbonyl; R$^{13}$, R$^{15}$, R$^{16}$, R$^{17}$, R$^{18}$, R$^{19}$, R$^{20}$, R$^{21}$ and R$^{23}$ are each independently hydrogen, C$_{1-6}$alkyl, hydroxy, mercapto, C$_{1-6}$alkyloxy, C$_{1-6}$alkylthio, halo and (C$_{1-6}$alkyloxycarbonyl)C$_{1-6}$alkyl;

G$^1$ is —CH=CH—CH=CH—, —S—CH=CH— or —N=CH—NH—;

G$^2$ is —CH=CH—CH=CH—, —S—(CH$_2$)$_2$—, —S—(CH$_2$)$_3$—, —(CH$_2$)$_4$—, —S—CH=CH—, —HN—CH=CH—, —NH—(CH$_2$)$_2$— or —NH—(CH$_2$)$_3$—;

G$^3$ is —CH=CH—CH=CH—, —CH$_2$—NH—(CH$_2$)$_2$—, —S—CH=CH—, —S—(CH$_2$)$_3$—, —N=CH—CH=CH—, —CH=N—CH=CH—, —CH=CH—N=CH—, —CH=CH—CH=N—, —N=CH—N=CH— or —CH=N—CH=N—;

G$^4$ is —CH=CH—CH=CH—, —CH$_2$—NH—(CH$_2$)$_2$—, —N=CH—CH=CH—, —CH=N—CH=CH—, —CH=CH—N=CH—, —CH=CH—CH=N—, —N=CH—N=CH— or —CH=N—CH=N—;

G$^5$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

$G^6$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

wherein one or two hydrogen atoms in said radicals $G^1$, $G^2$, $G^3$, $G^4$, $G^5$ or $G^6$ or in the benzene part of the radicals of formula (c-2) or (c-3) may be replaced by $C_{1-6}$alkyl, $C_{1-6}$alkylthio, $C_{1-6}$alkyloxy or halo where said hydrogen atom is bonded on a carbon atom, or by $C_{1-6}$alkyl, $C_{1-6}$alkyloxycarbonyl, $Ar^2$—$C_{1-6}$alkyl, where said hydrogen is bonded on a nitrogen atom;

An interesting subgroup among the compounds of formula (I) comprises those compounds of formula (I) wherein —$A^1$=$A^2$—$A^3$=$A^4$— is a bivalent radical having a formula (a-1) through (a-4), with (a-1) being the most interesting subgroup.

Another interesting subgroup among the compounds of formula (I) comprises those compounds of formula (I) wherein —$A^1$=$A^2$—$A^3$=$A^4$— is a bivalent radical having the formula (a-5) or (a-6).

Among the above subgroups those compounds of formula (I) are preferred wherein Het is the particular Het described hereinabove.

Particularly preferred compounds within the invention are those preferred compounds of formula (I) wherein $R^1$ is $C_{1-6}$alkyl substituted with $Ar^1$ or wherein $R^1$ is a radical —Alk—O—$R^2$, said $R^2$ being hydrogen, $C_{1-6}$alkyl, $C_{2-6}$alkenyl, $C_{3-6}$alkynyl or $Ar^1$.

More particularly preferred compounds within the invention are those particularly preferred compounds wherein R is hydrogen, m is 1, n is 1, and L is hydrogen, $C_{1-6}$alkyl or a radical of formula (b-1),(b-2) or (b-3).

Especially preferred compounds are those more particularly preferred compounds wherein $R^4$ is $Ar^2$ or Het, $R^5$ and $R^6$ are $C_{1-4}$alkyl, $Ar^2$ or Het, $R^8$ is hydrogen or $C_{1-4}$alkyl, X is O or S, and $Z^1$ and $Z^2$ are each independently NH or a direct bond.

More especially preferred compounds are those especially preferred compounds wherein $R^1$ is an ethoxyethyl radical.

The compounds of formula (I) can generally be prepared by cyclizing either an intermediate of formula (II-a) or an intermediate (II-b).

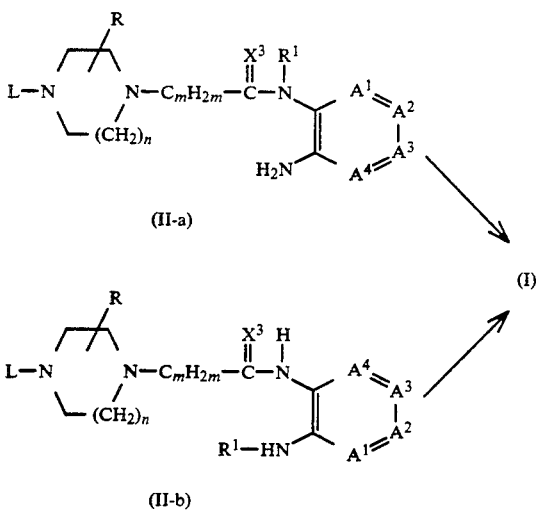

In (II-a) and (II-b) $X^3$ denotes O, S or NH. The cyclization reaction of (II-a) or (II-b) may be conducted in a suitable solvent such as, for example, a hydrocarbon, e.g., benzene, methylbenzene, dimethylbenzene, hexane and the like; an ether, e.g., 1,1'-oxybisethane, tetrahydrofuran and the like; a ketone, e.g., 2-propanone, 2-butanone and the like; an alcohol, e.g., methanol, ethanol, 2-propanol, 1-butanol and the like; a halogenated hydrocarbon, e.g., trichloromethane, dichloromethane and the like, a polar aprotic solvent, e.g., N,N-dimethylformamide, N,N-dimethylacetamide and the like; an organic acid, e.g., acetic acid, propanoic acid and the like; an aqueous solution of a mineral acid, e.g., hydrochloric acid and the like; and mixtures of such solvents. In order to enhance the reaction rate, it may be advantageous to heat the reaction mixture, preferably to the reflux temperature of the reaction mixture.

In some instances, especially where $X^3$ is O, the cyclization reaction of (II-a) or (II-b) may be conducted in the presence of a suitable dehydrating agent such as, for example, polyphosphoric acid, phosphorous pentoxide, phosphoryl chloride, pentachlorophosphorane, 4-methylbenzenesulfonic acid and the like.

According similar cyclization procedures as described above compounds of formula (I) may be prepared by reacting an acid of formula (IV) or a functional derivative thereof with a diamine of formula (III).

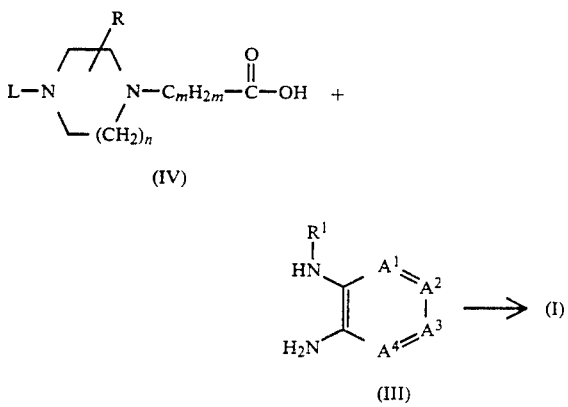

Said functional derivative of (IV) is meant to comprise the halide, anhydride, amide, and ester form of (IV), including the ortho and imino ester form thereof.

In a preferred method of conducting the above reaction there is used an imino ester form of (IV). The desired compounds of formula (I), are thus prepared by stirring the reactants at room temperature or at an elevated temperature in an acidic medium such as, for example, acetic acid, or a lower alkanol, whereto an appropriate acid, e.g., hydrochloric acid has been added. However, when the imino ester is in the form of an acid addition salt there is no need for adding additional acid. Depending on the nature of (IV) and the reaction conditions, intermediates of formulae (II-a) or (II-b) may be generated, which may in situ, or if desired, after isolation and purification, by cyclized to obtain the compounds of formula (I).

The compounds of formula (I) can also be obtained by reacting a piperazine or hexahydro-1H-1,4-diazepine derivative of formula (V) with an imidazopyridine or imidazopyrimidine derivative of formula (VI) following art-known N-alkylation procedures.

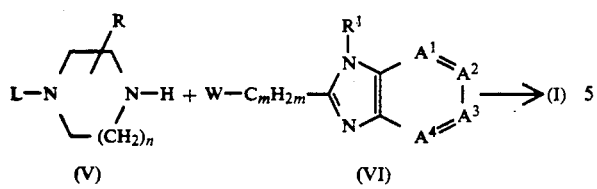

In the reaction of (V) with (VI) and in the following reaction schemes W represent and appropriate leaving group such as, for example, halo, e.g., chloro, bromo or iodo, or a sulfonyloxy group, e.g., methylsulfonyloxy or 4-methylphenylsulfonyloxy.

Said N-alkylation reaction of (V) with (VI) may conveniently be conducted by stirring the reactants in the presence of a suitable organic solvent such as, for example, an aromatic hydrocarbon, e.g., benzene, methylbenzene, dimethylbenzene, and the like; a ketone, e.g., 2-propanone, 4-methyl-2-pentanone and the like; an ether, e.g., 1,4-dioxane, 1,1'-oxybisethane, tetrahydrofuran and the like; a polar aprotic solvent, e.g., N,N-dimethylformamide, N,N-dimethylacetamide, dimethyl sulfoxide, 1-methyl-2-pyrrolidinone, acetonitrile, hexamethylphosphor triamide, 1,3-dimethyl-3,4,5,6-tetrahydro-2(1H)-pyrimidinone, 1,3-dimethyl-2-imidazolidinone, benzonitrile and the like; an excess of (V); and mixtures of such solvents. Somewhat elevated temperatures may b appropriate to enhance the rate of the reaction and in some cases the reaction may even be carried out at the reflux temperature of the reaction mixture. The addition of an appropriate base such as, for example, an alkali or an earth alkaline metal carbonate, hydrogen carbonate, hydroxide, amide or hydride, e.g., sodium hydroxide, potassium hydroxide, potassium carbonate, sodium hydride and the like or an organic base, such as, for example, N,N-dimethyl-4-pyridinamine, pyridine, N,N-diethylethanamine or N-(1-methylethyl)-2-propanamine may be employed to pick up the acid which is liberated during the courses of the reaction.

The compounds of formula (I) may also be prepared by reacting a piperazine or hexahydro-1H-1,4-diazepine derivative of formula (V) with the corresponding carbonyl-oxidated form of the imidazopyridine or imidazopyrimidine derivative of formula (VI), following art-known reductive N-alkylation procedures.

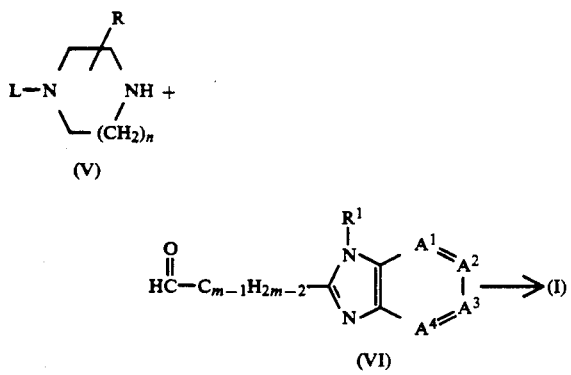

Said reductive N-alkylation reaction may conveniently be carried out by catalytically hydrogenating a stirred and/or heated mixture of the reactants in a suitable reaction inert organic solvent according to art-known catalytic hydrogenating procedures. Suitable solvents are, for example, water; alkanols, e.g., methanol, etha- nol, 2-propanol and the like; cyclic ethers, e.g., 1,4-dioxane and the like; halogenated hydrocarbons, e.g., trichloromethane and the like; N,N-dimethylformamide; dimethyl sulfoxide and the like; or a mixture of such solvents. The term "art-known catalytic hydrogenating procedures" means that the reaction is carried out under hydrogen atmosphere in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) may further be synthesized by reacting a piperazine or hexahydro-1H-1,4-diazepine derivative of formula (VIII) with an imidazopyridine or imidazopyrimidine of formula (IX) or preferably with the corresponding two metal substitution form of (IX).

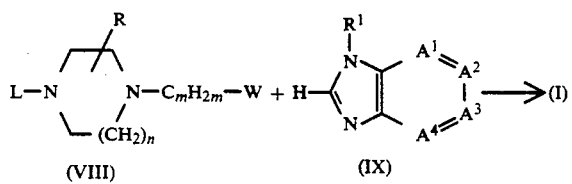

The alkylation reaction of (VIII) with (IX) may be carried out in the usual manner, e.g. by stirring the reactants at ambient or lower temperatures in an appropriate organic solvent such as, for example, an ether, e.g. 1,4-dioxane, 1,1'-oxybisethane, tetrahydrofuran; a halogenated hydrocarbon, e.g., trichloromethane; and the like.

The compounds of formula (I) can also be converted into each other. Some examples of such conversions will be described hereinafter.

The compounds of formula (I) wherein $R^1$ is other than hydrogen, said radical being represented by $R^{1-a}$ and said compounds by formula (I-a), can be prepared by N-alkylating a compound of formula (I-b) with an appropriate reagent of formula (X) according to the hereinbefore described N-alkylation procedures.

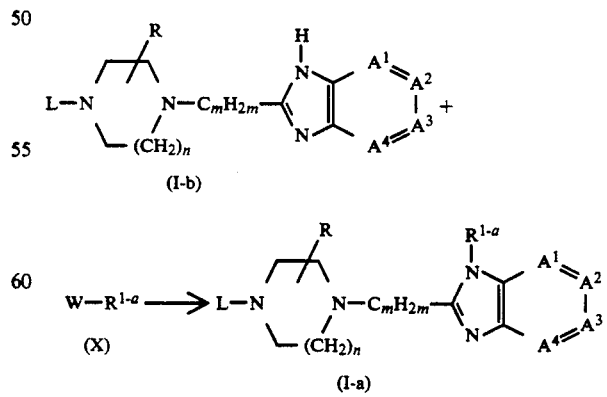

In order to simplify the structural representations of the compounds of formula (I) and of certain precursors and intermediates thereof the

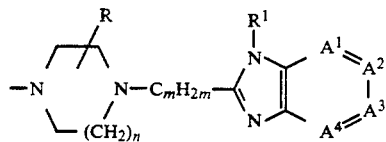

radical will hereafter be represented by the symbol D.

The compounds of formula (I) wherein L is other then hydrogen, said L being represented by $L^1$, and said compounds being represented by formula (I-c) can generally be prepared by N-alkylating a compound of formula (I) wherein L is hydrogen, said compounds being represented by formula (I-d), with a reagent of formula (XI).

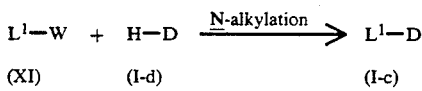

Said N-alkylation is conveniently carried out according to art-known N-alkylation procedures described hereinabove for the preparation of (I) starting from (V) and (VI).

The compounds of formula (I) wherein L is $C_{3-6}$cycloalkyl, $C_{1-12}$alkyl, a radical of formula (b-1), (b-2) or (b-3) said radical L being represented by the radical $L^2H-$, and said compounds being represented by formula (I-c-1) can also be prepared by the reductive N-alkylation reaction of (I-d) with an appropriate ketone or aldehyde of formula $L^2=O$ (XII), said $L^2=O$ being an intermediate of formula $L^2H_2$ wherein two geminal hydrogen atoms are replaced by $=O$, and $L^2=$ is a geminal bivalent radical comprising $C_{3-6}$cycloalkylidene, $C_{1-12}$alkylidene, $R^4-C_{1-6}$alkylidene, $R^5-Y-C_{1-6}$alkylidene and $R^6-Z^2-C(=X)-Z^1-C_{1-6}$alkylidene.

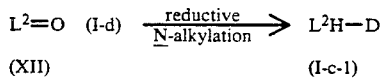

Said reductive N-alkylation is conveniently carried out according to art-known reductive N-alkylation procedures described hereinabove for the preparation of (I) starting from (V) and (VII).

The compounds of formula (I) wherein L is a radical of formula (b-2) wherein $R^5$ is $Ar^2$ or Het, said $R^5$ being represented by $R^{5-a}$ and said compounds by formula (I-c-2) may also be prepared by alkylating a compound of formula (I) wherein L is a radical of formula (b-2) wherein $R^5$ is hydrogen, said compounds being represented by formula (I-c-3), with a reagent of formula (XIII).

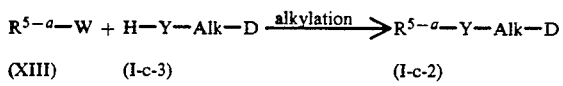

The compounds of formula (I-c-2) can also be prepared by alkylating a compound of formula (I-c-4) with a reagent of formula (XIV).

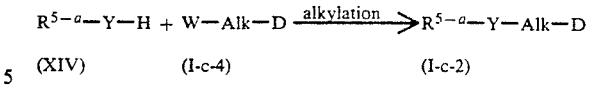

The alkylation reactions of (XIII) with (I-c-3) and (XIV) with (I-c-4) may conveniently be conducted in an inert organic solvent such as, for example, an aromatic hydrocarbon, e.g., benzene, methylbenzene, dimethylbenzene; a ketone, e.g., 2-propanone, 4-methyl-2-pentanone; an ether, e.g., 1,4-dioxane, 1,1'-oxybisethane, tetrahydrofuran; and a polar aprotic solvent, e.g., N,N-dimethylformamide; N,N-dimethylacetamide; dimethyl sulfoxide; nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein L is a radical of formula (b-3) wherein $Z^1$ is NH and $Z^2$ is other than a direct bond, said $Z^2$ being represented by $Z^{2-a}$, and said compounds by (I-c-5) can be prepared by reacting an isocyanate or isothiocyanate of formula (I-c-6) with a reagent of formula (XV).

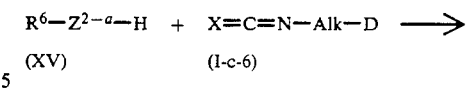

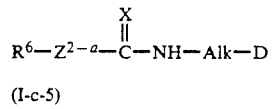

The compounds of formula (I) wherein L is a radical of formula (b-3) wherein $Z^2$ is NH and $Z^1$ is other than a direct bond, said $Z^1$ being represented by $Z^{1-a}$ and said compounds by (I-c-7), can be prepared by reacting a isocyanate or isothiocyanate of formula (XVI) with a compound of formula (I-c-8).

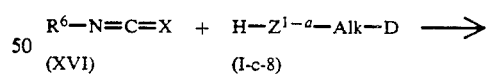

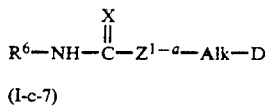

The reaction of (XV) with (I-c-6), or (XVI) with (I-c-8) is generally conducted in a suitable reaction-inert solvent such as, for example, an ether, e.g., tetrahydrofuran and the like. Elevated temperatures may be suitable to enhance the rate of the reaction.

The compounds of formula (I) wherein L is a radical of formula (b-3) wherein $Z^2$ is a direct bond and $Z^1$ is other than a direct bond, said compounds being represented by (I-c-9), can be prepared by reacting a reagent of formula (XVII) or a functional derivative thereof with a compound of formula (I-c-8).

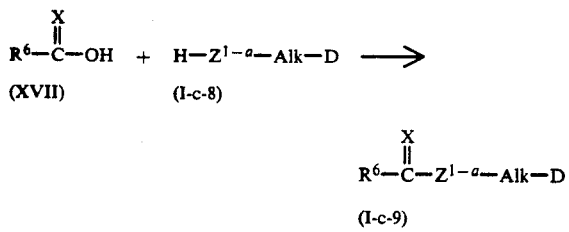

(XVII)  (I-c-8)

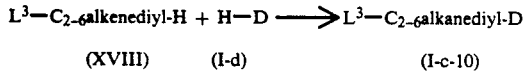

(I-c-9)

The reaction of (XVII) with (I-c-8) may generally be conducted following art-known esterification- or amidation reaction procedures. For example, the carboxylic acid may be converted into a reactive derivative, e.g., an anhydride or a carboxylic acid halide, which subsequently is reacted with (I-c-8); or by reacting (XVII) and (I-c-8) with a suitable reagent capable of forming amides or esters, e.g., N,N-methanetetraylbis[cyclohexamine], 2-chloro-1-methylpyridinium iodide and the like. Said reactions are most conveniently conducted in a suitable solvent such as, for example, an ether, e.g., tetrahydrofuran, a halogenated hydrocarbon, e.g., dichloromethane, trichloromethane or a polar aprotic solvent. The addition of a base such as, N,N-diethylethanamine may be appropriate.

The compounds of formula (I) wherein L is a radical of formula $L^3$—$C_{2-6}$alkanediyl, said $L^3$ being $Ar^2$, Het, $Ar^2$—sulfonyl or a radical of formula $R^6$—$Z^2$—C(=X)—, and said compounds being represented by formula (I-c-10), may also be prepared by reacting an appropriate alkenylene of formula (XVIII) with a compound of formula (I-d).

$L^3$—$C_{2-6}$alkenediyl-H + H—D ⟶ $L^3$—$C_{2-6}$alkanediyl-D (XVIII)  (I-d)  (I-c-10)

The compounds of formula (I) wherein L is a radical of formula (b-4) or a 2-hydroxyethyl, said compounds being represented by formula (I-c-11), may also be prepared by reacting a reagent (XIX) with a compound of formula (I-d).

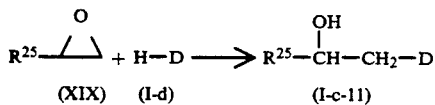

(XIX)  (I-d)  (I-c-11)

$R^{25}$ in (XIX) and (I-c-11) being hydrogen or a radical $R^7$—O—$CH_2$—. The reactions of (XVIII) with (I-d) and (XIX) with (I-d) may be conducted by stirring and, if desired, heating the reactants. The said reactions may be conducted in a suitable solvent such as, for example, a ketone, e.g., 2-propanone, 4-methyl-2-pentanone, an ether, e.g., tetrahydrofuran, 1,1′-oxybisethane, an alcohol, e.g., methanol, ethanol, 1-butanol, a polar aprotic solvent, e.g., N,N-dimethylformamide, N,N-dimethylacetamide, and the like.

The compounds of formula (I) wherein $R^4$, $R^5$ or $R^6$ are Het, may also be prepared following procedures for preparing ring systems which are known in the art or analogues procedures thereof. A number of such cyclization procedures are described in for example, the Published European Patent Publication No. 151,826, incorporated herein by reference. For example, compounds of formula (I-c-12) can be obtained by a cyclizing reaction of (I-c-13) following art-known cyclodesulfurization procedures.

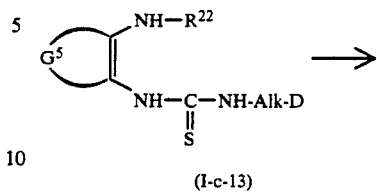

(I-c-13)

(I-c-12)

In (I-c-13) and (I-c-12) $G^5$ and $R^{22}$ have the same meanings as described hereinbefore.

Compounds wherein Het is an optionally substituted imidazolyl radical, said compounds being represented by the formula (I-c-13), can be prepared by the cyclization reaction of an appropriate N-(2,2-dilower alkyloxyethyl)guanidine derivative of formula (XX).

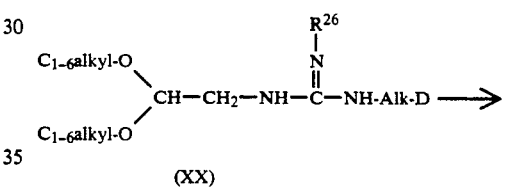

(XX)

(I-c-14)

In (XX) and (I-c-14) $R^{26}$ is either hydrogen, $C_{1-6}$alkyl or $Ar^2$—$C_{1-6}$alkyl.

The compounds of formula (I) can also be converted into each other following art-known procedures of functional grouptransformation. Some examples of such procedures will be cited hereinafter.

The compounds of formula (I) containing a cyano substituent can be converted into the corresponding amines by stirring and, if desired, heating the starting cyano compounds in a hydrogen containing medium in the presence of a suitable amount of an appropriate catalyst such as, for example, platinum-on-charcoal, Raney-nickel and the like catalyst. Suitable solvents are, for example, methanol, ethanol and the like.

The hydrogen atoms of the amino function(s) of compounds of formula (I) may be substituted following art-known procedures such as, for example, N-alkylation, N-acylation, reductive N-alkylation and the like methods. For example alkylcarbonyl, arylcarbonyl and the like groups may be introduced by reacting the starting amine with an appropriate carboxylic acid or a derivative thereof such as, for example, an acid halide, acid anhydride and the like.

The compounds of formula (I) containing a substituted amine may be converted into the corresponding compounds of formula (I) wherein said nitrogen bears a hydrogen atom following art-known methods for preparing NH groups. For example, where said amine is substituted with a $C_{1-6}$alkyloxycarbonyl group by treating the starting material with an acid or a base in a suitable solvent. As suitable acids there may be cited hydrohalic acids, e.g., hydrochloric acid or hydrobromic acid, sulfuric, phosphoric and the like acids preferably employed as an aqueous solution or mixed with, e.g., acetic acid. Suitable bases are the alkali metal hydroxides, hydrides or alkoxides in an aqueous or alcoholic medium. Or, where said nitrogen is substituted with an $Ar^2$—$CH_2$ group, by treating the starting compounds with hydrogen in the presence of a suitable catalyst, e.g., palladium-on-charcoal, platinum-on-charcoal, preferably in an alcoholic medium.

The compounds of formula (I) containing a nitrogen atom substituted with $Ar^2$—$CH_2$— may also be converted into the corresponding compounds where said nitrogen is substituted with $C_{1-6}$alkyloxycarbonyl, for example by treating the former compounds with a $C_{1-6}$alkylcarbonohalidate, e.g., ethyl carbonochloridate in the presence of a suitable solvent, e.g., methylbenzene and, if desired, in the presence of an appropriate base.

The compounds of formula (I) wherein the piperazine or hexahydro1H-1,4-diazepine nitrogen is substituted with a $C_{1-6}$alkyloxycarbonyl group may be converted into the corresponding compounds wherein the ring nitrogen is substituted with methyl by reducing the starting compounds with an appropriate reductant such as, lithium tetrahydroaluminate.

The compounds of formula (I) containing an amino group may be converted into the corresponding isothiocyanato containing compounds by treating the starting amino compounds with $CS_2$ optionally in the presence of N,N-methanetetraylbis[cyclohexamine].

In all of the foregoing and in the following preparations, the reaction products may be isolated from the reaction mixture and, if necessary, further purified according to methodologies generally known in the art.

Some intermediates and starting materials in the foregoing preparations are known compounds which may be prepared according to art-known methodologies of preparing said or similar compounds and others are new. A number of such preparation methods will be described hereinafter in more detail.

Intermediates of formula (II-a) may be prepared by reacting a piperazine or hexahydro-1H-1,4-diazepine derivative of formula (V) with an appropriately substituted nitro-pyridine or -pyrimidine of formula (XXI), thus preparing (XXII), and subsequently reducing the nitro function.

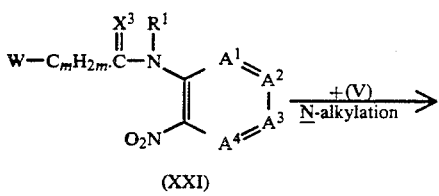

(XXI)

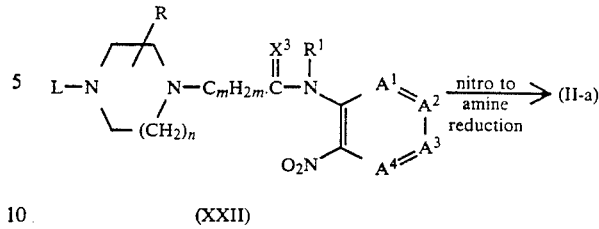

(XXII)

Whereas the intermediates of formula (II-b) may be prepared by reacting a piperazine or hexahydro-1H-1,4-diazepine derivative of formula (V) with an appropriately substituted diamine of formula (XXIII).

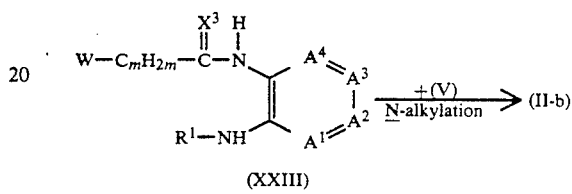

(XXIII)

The N-alkylation reactions of (V) with (XXI) and (V) with (XXIII) may be carried out following the N-alkylation procedures described for the preparation of (I) starting from (V) and (VI).

The nitro-to-amine reduction reaction is generally carried out by stirring an intermediate of formula (XXI) in a hydrogen containing medium in the presence of a suitable amount of an appropriate catalyst such as, for example, platinum-on-charcoal, palladium-on-charcoal, Raney-nickel and the like. Suitable solvents are, for example, an alcohol, e.g., methanol, ethanol, 2-propanol, 1-butanol and the like.

Intermediates of formula (VI) can be prepared by condensing an appropriately substituted pyridinediamine or pyrimidinediamine of formula (III) with an carbonic acid of formula (XXIV) or a suitable functional derivative thereof, preferably the imino ester form thereof, following the procedures for preparing (I) from (IV) and (III).

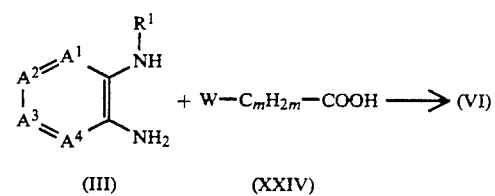

(III)  (XXIV)

The starting materials of formula (III) can be prepared by reacting a nitro-pyridine or -pyrimidine of formula (XXV) with an amide of formula (XXVI) and subsequently reducing the nitro function.

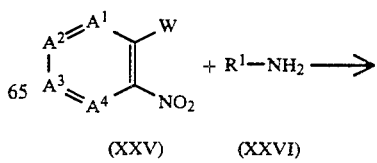

(XXV)  (XXVI)

-continued $$\underset{(XXVII)}{\overset{A^2=A^1}{\underset{A^3\diagdown A^4}{|}}\diagdown\overset{NH-R^1}{\underset{NO_2}{}}} \longrightarrow (III)$$

The starting materials of formula (XXIII) and (XXI) can be prepared by reacting an appropriately substituted pyridinediamine or pyrimidinediamine of formula (III) or their corresponding nitro analogue of formula (XXVII) with a carbonic acid of formula (XXIV), preferably the halide form thereof.

The intermediates of formula (V) wherein L is other than hydrogen, said compounds being represented by formula (V-a), can be prepared by N-alkylating a protected piperazine or hexahydro-1H-1,4-diazepine of formula (XXVIII) with a reagent of formula $L^1$—W (XI), thus preparing an intermediate (XXIX), and subsequently removing the protected group P following art-known procedures, e.g. by hydrolysis in an acidic or an alkaline aqueous medium or by catalytic hydrogenation, depending upon the nature of P.

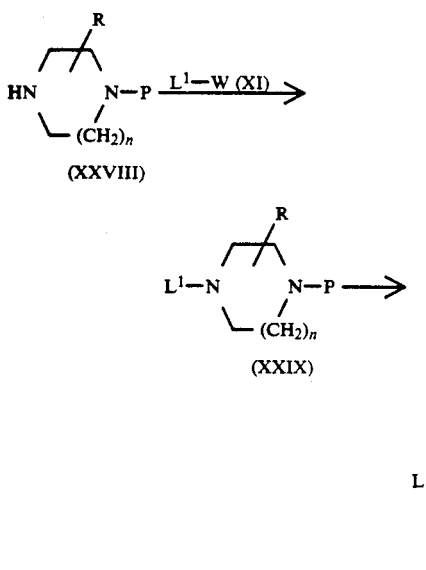

In (XXVIII) P is an appropriate protected group such as, for example, $C_{1-6}$alkyloxycarbonyl, phenylmethoxycarbonyl, phenylmethyl and the like.

From formula (I) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, (1966).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The compounds of formula (I), the pharmaceutically acceptable acid addition salts and possible stereochemically isomeric forms thereof possess useful pharmacological properties. More particularly, they are active as anti-histaminics which activity can clearly be demonstrated by, e.g., the results obtained in the "Protection of Rats from Compound 48/80-induced lethality"-test, the "Histamine antagonism in Guinea Pig"-test and the "Ascaris Allergy test in Dogs"-test described in Arch. Int. Pharmacodyn. Ther. 251, 39–51 (1981). Apart from their anti-histaminic properties some of the subject compounds also show serotonin-antagonism. Furthermore the compounds of formula (I), the pharmaceutically acceptable acid addition salts and stereochemically isomeric forms thereof are particularly attractive due to their favourable pharmacokinetical profile and high selectivity. In particularly, they show a rapid onset so that their anti-histaminic effects are almost instantaneously present.

In view of their anti-histaminic properties, the compounds of formula (I) and their acid addition salts are very useful in the treatment of allergic diseases such as, for example, allergic rhinitis, allergic conjunctivities, chronic urticaria, allergic astma and the like.

In view of their useful pharmacological properties the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in treating allergic diseases in warm-blooded animals could easily determine the effective amount from the test results presented hereinafter. In general it is contemplated that an effective amount would be from 0.001 mg/kg to 100 mg/kg body weight, and more preferably from 0.01 mg/kg to 1 mg/kg body weight.

The following examples are intented to illustrate and not to limit the scope of the present invention in all its aspects. Unless otherwise stated all parts therein are by weight.

Experimental Part

A. Intermediates

Example 1 a) To a stirred solution of 42.24 parts of N-(2-ethoxyethyl)-3-nitro-2-pyridinamine in 309 parts of 1,4-dioxane were added 49.7 parts of 2-chloroacetyl chloride. The reaction mixture was stirred for 4 hours at reflux temperature. The whole was evaporated and the residue was taken up in methylbenzene. The organic layer was evaporated again, yielding 57.5 parts (100%) of 2-chloro-N-(2-ethoxyethyl)-N-(3-nitro-2-pyridinyl)acetamide as a residue (int. 1).

b) A solution of 19.3 parts of 2-chloro-N-(2-ethoxyethyl)-N-(3-nitro-2-pyridinyl)acetamide, 11.4 parts of ethyl 1-piperazinecarboxylate and 7.63 parts of sodium carbonate in 270 parts of methylbenzene was stirred for 18 hours at 80° C. The reaction mixture was evaporated and the residue was taken up in water and dichloromethane. The organic layer was dried, filtered and evaporated. The residue was purified by column chromatography over silica gel using a mixture of trichloromethane and methanol (99:1 by volume) as eluent. The pure fractions were collected and the eluent was evaporated, yielding 16.7 parts (60.9%) of ethyl 4-[2-[(2-ethoxyethyl)(3-nitro-2-pyridinyl)amino]-2-oxomethyl]-1-piperazinecarboxylate as a residue (int. 2).

In a similar manner there were also prepared:

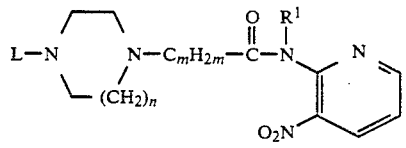

| Int. No. | L | n | m | $R^1$ | physical properties |
|---|---|---|---|---|---|
| 3 | $H_3C-CH_2-O-\overset{O}{\underset{\|}{C}}-$ | 1 | 1 | $-CH_2-\text{(furan-CH}_3\text{)}$ | residue |
| 4 | $H_3C-$ | 1 | 1 | $-CH_2-\text{(furan)}$ | residue |
| 5 | $H_3C-$ | 1 | 1 | $-CH_2-\text{(thiazole)}$ | residue |
| 6 | $H_3C-$ | 2 | 1 | $-(CH_2)_2-O-CH_2-CH_3$ | residue |
| 7 | $H_3C-$ | 1 | 1 | $-(CH_2)_2-O-CH_2-C_6H_5$ | residue |
| 8 | $C_6H_5-CH_2-$ | 2 | 1 | $-(CH_2)_2-O-CH_2-CH_3$ | residue |
| 9 | $H_3C-$ | 1 | 1 | $-CH_2-\text{(furan-CH}_3\text{)}$ | residue |

-continued

| Int. No. | L | n | m | R¹ | physical properties |
|---|---|---|---|---|---|
| 10 | H₃C—CH₂—O—C(=O)— | 1 | 1 | —CH₂-(3-methylfuran-2-yl) | residue |
| 11 | H₃C—CH₂—O—C(=O)— | 1 | 2 | —(CH₂)₂—O—CH₂—CH₃ | residue |
| 12 | C₆H₅—CH₂— | 1 | 3 | —(CH₂)₂—O—CH₂—CH₃ | residue |
| 13 | C₆H₅—CH₂— | 1 | 4 | —(CH₂)₂—O—CH₂—CH₃ | residue |

Example 2

A mixture of ethyl 4-[2-[(2-ethoxyethyl)(3-nitro-2-pyridinyl)amino]-2-oxomethyl]-1-piperazinecarboxylate, 2 parts of a solution of thiophene in methanol 4% and 200 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated, yielding 15.2 parts (100%) of ethyl 4-[2-[(3-amino-2-pyridinyl)(2-ethoxyethyl)amino]-2-oxomethyl]-1-piperazinecarboxylate as a residue (int. 14).

In a similar manner there were also prepared:

| Int. No. | L | n | m | R¹ | physical properties |
|---|---|---|---|---|---|
| 15 | H₃C—CH₂—O—C(=O)— | 1 | 1 | —CH₂-(5-methylfuran-2-yl) | residue |
| 16 | H₃C— | 1 | 1 | —CH₂-(furan-2-yl) | residue |
| 17 | H₃C— | 1 | 1 | —CH₂-(thiazol-4-yl) | residue |
| 18 | H₃C— | 2 | 1 | —(CH₂)₂—O—CH₂—CH₃ | residue |
| 19 | H₃C— | 1 | 1 | —(CH₂)₂—O—CH₂—C₆H₅ | residue |
| 20 | C₆H₅—CH₂— | 2 | 1 | —(CH₂)₂—O—CH₂—CH₃ | residue |
| 21 | H₃C— | 1 | 1 | —CH₂-(3-methylfuran-2-yl) | residue |
| 22 | H₃C—CH₂—O—C(=O)— | 1 | 1 | —CH₂-(3-methylfuran-2-yl) | residue |
| 23 | H₃C—CH₂—O—C(=O)— | 1 | 2 | —(CH₂)₂—O—CH₂—CH₃ | residue |

Example 3 a) To a stirred solution of 3.8 parts of N³-(2-ethoxyethyl)-2,3-pyridinediamine in 50 parts of 1,4-dioxane were added 5.64 parts of 2-chloroacetyl chloride. The reaction mixture was stirred for 5 hours at reflux temperature. The reaction mixture was evaporated and the residue was dissolved in methylbenzene. The whole was evaporated again, yielding 3.62 parts (70.4%) of 2-chloro-N-[3-[(2-ethoxyethyl)amino]-2-pyridinyl]acetamide as a residue (int. 24).

b) A mixture of 3.62 parts of 2-chloro-N-[3-[(2-ethoxyethyl)amino]-2-pyridinyl]acetamide, 10.6 parts of 1-(phenylmethyl)piperazine, 6.4 parts of sodium carbonate and 90 parts of methylbenzene was stirred for 20 hours at 80° C. The reaction mixture was evaporated and the residue was taken up in water. The product was extracted with dichloromethane. The extract was dried, filtered and evaporated, yielding 7.9 parts (100%) of N-[3-[(2-ethoxyethyl)amino]-2-pyridinyl]-4-(phenylmethyl)-1-piperazineacetamide as a residue (int. 25).

In a similar manner there was also prepared: N-[3-[(2-ethoxyethyl)amino]-4-pyridinyl]-4-(phenylmethyl)-1-piperazineacetamide as a residue (int. 26).

Example 4 a) To a stirred solution of 25.4 parts of 2-chloro-3-nitropyridine, 29.5 parts of 2-pyrazinemethanamine dihydrochloride and 235 parts of N,N-dimethylacetamide were added 67.8 parts of sodium carbonate. The reaction mixture was stirred for 1.5 hours at 100° C. The reaction mixture was poured into water and 4-methyl-2-pentanone. The whole was filtered twice over diatomaceous earth and the layers were separated. The organic layer was dried, filtered and evaporated. The residue was crystallized from acetonitrile. The product was filtered off and dried, yielding 3.6 parts (10%) of N-(3-nitro-2-pyridinyl)-2-pyrazinemethanamine (int. 27).

b) A mixture of 3.55 parts of N-(3-nitro-2-pyridinyl)-2-pyrazinemethanamine, 2 parts of a solution of thiophene in methanol 4% and 120 parts of methanol was hydrogenated at normal pressure and at room temperature with 2 parts of platinum-on-charcoal catalyst 5%. After the calculated amount of hydrogen was taken up, the catalyst was filtered off and the filtrate was evaporated to dry, yielding 3.6 parts (100%) of N-(2-pyrazinylmethyl)-1,2-pyridinediamine as a residue (int 28).

c) To a stirred solution of 3.6 parts of N-(2-pyrazinylmethyl)-1,2-pyridinediamine in 30 parts of acetic acid were added 4.24 parts of ethyl 2-chloroethanimidate monohydrochloride. The reaction mixture was stirred first for 21 hours at room temperature and then for a few minutes at 90° C. The whole was evaporated and the residue was taken up in water. The aqueous layer was treated with sodium carbonate and the product was extracted with dichloromethane. The extract was dried, filtered and evaporated, yielding 3.9 parts (100%) of 2-(chloromethyl)-3-(2-pyrazinylmethyl)-3H-imidazo[4,5-b]pyridine as a residue (int. 29).

In a similar manner there were also prepared:
8-(chloromethyl)-9-(2-ethoxyethyl)-9H-purine as a residue (int. 30); and
2-(chloromethyl)-3H-imidazo[4,5-b]pyridine-3-ethanol; mp. 136.2° C. (int. 31).

B. Final Compounds

Example 5

A mixture of 10.6 parts of N-(3-amino-2-pyridinyl)-N-(2-furanylmethyl)-4-methyl-1-piperazineacetamide, 0.1 parts of 4-methylbenzenesulfonic acid and 95 parts of dimethylbenzene was stirred for 40 hours at reflux temperature using a water separator. The reaction mixture was evaporated and the residue was taken up in dichloromethane and a diluted sodium hydroxide solution. The separated organic layer was dried, filtered and evaporated. The residue was purified by column chromatography over silica gel using a mixture of trichloromethane and methanol, saturated with ammonia (95:5 by volume) as eluent. The pure fractions were collected and the eluent was evaporated. The residue was converted into the (E)-2-butenedioate salt in 2-propanol. The salt was filtered off and dried, yielding 4.34 parts (26.6%) of 3-(2-furanylmethyl)-2-[(4-methyl-1-piperazinyl)methyl]-3H-imidazo-[4,5-b]pyridine (E)-2-butenedioate(1:2); mp. 124.5° C. (compound 1).

In a similar manner there were also prepared:
ethyl 4-[[3-[(5-methyl-2-furanyl)methyl]-3H-imidazo[4,5-b]pyridin-2-yl]methyl]-1-piperazinecarboxylate as a residue (compound 2);
2-[(4-methyl-1-piperazinyl)methyl]-3-(4-thiazolylmethyl)-3H-imidazo[4,5-b]pyridine (E)-2-butenedioate(1:1); mp. 175.9° C. (compound 3);
3-(2-ethoxyethyl)-2-[(hexahydro-4-methyl-1H-1,4-diazepin-1-yl)methyl]-3H-imidazo[4,5-b]pyridine (E)-2-butenedioate(1:2); mp. 153.4° C. (compound 4);
2-[(4-methyl-1-piperazinyl)methyl]-3-[2-(phenylmethoxy)ethyl]-3H-imidazo[4,5-b]pyridine (E)-2-butenedioate(1:2); mp. 162.6° C. (compound 5);
ethyl 4-[[1-(2-ethoxyethyl)-3H-imidazo[4,5-b]pyridin-2-yl]methyl]-1-piperazinecarboxylate as a residue (compound 6);
3-(2-ethoxyethyl)-2-[[hexahydro-4-(phenylmethyl)-1H-1,4-diazepin-1-yl]-methyl]-3H-imidazo[4,5-b]pyridine ethanedioate(1:2); mp. 136° C. (compound 7);
3-[(3-methyl-2-furanyl)methyl]-2-[(4-methyl-1-piperazinyl)methyl]-3H-imidazo[4,5-b]pyridine (E)-2-butenedioate(1:2); mp. 186.5° C. (compound 8);
ethyl 4-[[3-(3-methyl-2-furanyl)methyl]-3H-imidazo[4,5-b]pyridin-2-yl]methyl]-1-piperazinecarboxylate as a residue (compound 9); and
ethyl 4-[2-[3-(2-ethoxyethyl)-3H-imidazo[4,5-b]pyridin-2-yl]ethyl]-1-piperazinecarboxylate as a residue (compound 10).

Example 6

A mixture of 37.8 parts of N-[3-[(2-ethoxyethyl)amino]-4-pyridinyl]-4-(phenylmethyl)-1-piperazineacetamide, 0.1 parts of 4-methylbenzenesulfonic acid and 450 parts of dimethylbenzene was stirred for 16 hours at reflux temperature using a water separator. The reaction mixture was evaporated and the residue was purified by column chromatography over silica gel using a mixture of dichloromethane and methanol (93:7 by volume) as eluent. The pure fractions were collected and the eluent was evaporated, yielding 20.2 parts (56.1%) of 3-(2-ethoxyethyl)-2-[[4-(phenylmethyl)-1-piperazinyl]methyl]-3H-imidazo[4,5-c]pyridine as a residue (compound 11).

In a similar manner there was also prepared:
1-(2-ethoxyethyl)-2-[[4-(phenylmethyl)-1-piperazinyl]methyl]-1H-imidazo[4,5-b]pyridine as a residue (compound 12); and
2-[(4-cyclohexyl-1-piperazinyl)methyl]-3-(2-ethoxyethyl)-3H-imidazo[4,5-b]pyridine (E)-2-butenedioate(2:3); mp. 190.6° C. (compound 13).

Example 7

A mixture of 8.5 parts of 4-methyl-N-[(5-methyl-2-furanyl)methyl]-N-(3-nitro-2-pyridinyl)-1-piperazineacetamide, 2 parts of a solution of thiophene in methanol 4% and 2DO parts of methanol was hydrogenated at normal pressure and at room temperature with 2 parts of platinum-on-charcoal catalyst 5%. After the calculated amount of hydrogen was taken up, the catalyst was filtered off and the filtrate was evaporated. The residue was purified by column chromatography over silica gel using a mixture of trichloromethane and methanol (90:10 by volume) as eluent. The pure fractions were collected and the eluent was evaporated. The residue was further purified by column chromatograhy (HPLC) over silica gel using a mixture of dichloromethane, hexane, methanol and methanol, saturated with ammonia (50:45:5:0.5 by volume) as eluent. The pure fractions were collected and the eluent was evaporated. The residue was converted into the (E)-2-butenedioate salt in 2-propanol. The salt was filtered off and dried, yielding 3.49 parts (26.7%) of 3-[(5-methyl-2-furanyl)methyl]-2-[(4-methyl-1-piperazinyl)methyl]-3H-imidazo[4,5-b]pyridine (E)-2-butenedioate(1:2) (compound 14).

In a similar manner there were also prepared:
3-(2-ethoxyethyl)-2-[3-[4-(phenylmethyl)-1-piperazinyl]propyl]-3H-imidazo[4,5-b]pyridine as a residue (compound 15); and
3-(2-ethoxyethyl)-2-[4-(1-piperazinyl)butyl]-3H-imidazo[4,5-b]-pyridine (E)-2-butenedioate(1:2); mp. 148.2° C. (compound 16).

Example 8

A mixture of 3.35 parts of 2-(chloroethyl)-3-(2-ethoxyethyl)-3H-imidazo[4,5-a]pyridine monohydrochloride and 6 parts of 1-methylpiperazine was stirred for 1 hour at 100° C. The reaction mixture was evaporated and the residue was purified by column chromatography over silica gel using a mixture of trichloromethane and methanol, saturated with ammonia, (90:10 by volume) as eluent. The pure fractions were collected and the eluent was evaporated. The residue was taken up in 2,2'-oxybispropane and activated charcoal. The whole was filtered over diatomaceous earth and the filtrate was evaporated. The residue was converted into the (E)-2-butenedioate salt in 2-propanol. The salt was filtered off and crystallized from 2-propanol. The product was filtered off and dried, yielding 2.24 parts (44.4%) of 3-(2-ethoxyethyl)-2-[(4-methyl-1-piperazinyl)methyl]-3H-imidazo[4,5-b]pyridine (E)-2-butenedioate(1:1); mp. 165.8° C. (compound 17).

Example 9

To a stirred mixture of 13.5 parts of ethyl 1-piperazinecarboxylate and 160 parts of ethanol were added 18 parts of 2-(chloromethyl)-3H-imidazo[4,5-b]pyridine-3-ethanol. After the addition of 10.6 parts of sodium carbonate, the reaction mixture was stirred for 32 hours at reflux temperature. The whole was evaporated and the residue taken up in water. The product was extracted with dichloromethane. The extract was washed with water, dried, filtered and evaporated. The residue was purified by column chromatography over silica gel using a mixture of dichloromethane and methanol (95:5 by volume) as eluent. The pure fractions were collected and the eluent was evaporated. The residue was crystallized from 2,2'-oxybispropane. The product was filtered off and dried, yielding 17.5 parts (62.7%) of ethyl 4-[[3-(2-hydroxyethyl)-3H-imidazo-[4,5-b]pyridin-2-yl]methyl]-1-piperazinecarboxylate; mp. 117.4° C. (compound 18).

In a similar manner there were also prepared:
3-(2-ethoxyethyl)-2-[[2-methyl-4-(phenylmethyl)-1-piperazinyl]methyl]-3H-imidazo[4,5-b]pyridine; mp. 91.2° C. (compound 19); ethyl 4-[[3-(2-ethoxyethyl)-3H-imidazo[4,5-b]pyridin-2-yl]methyl]-2-methyl-1-piperazinecarboxylate ethanedioate(1:1); mp. 146.6° C. (compound 20);
3-(2-ethoxyethyl)-2-[[4-[[3-[(5-methyl-2-furanyl)methyl]-3H-imidazo[4,5-b]pyridin-2-yl]methyl]-1-piperazinyl]methyl]-3H-imidazo[4,5-b]pyridine (E)-2-butenedioate(1:2); mp. 200.1° C. (compound 21); and
2-[(4-methyl-1-piperazinyl)methyl]-3-(2-pyrazinylmethyl)-3H-imidazo[4,5-b]pyridine; mp. 119.9° C. (compound 22).

Example 10

A mixture of 4.4 parts of 1-(phenylmethyl)piperazine, 4.7 parts of 8-(chloromethyl)-9-(2-ethoxyethyl)-9H-purine, 2.1 parts of sodium hydrogen carbonate and 40 parts of ethanol was stirred and refluxed for 5 hours. The reaction mixture was evaporated and the residue was taken up in water. The product was extracted with trichloromethane. The extract was dried, filtered and evaporated. The residue was purified by column chromatography over silica gel using a mixture of trichloromethane and methanol (97:3 by volume) as eluent. The pure fractions were collected and the eluent was evaporated, yielding 4.6 parts (62.0%) of 9-(2-ethoxyethyl)-8-[[4-(phenylmethyl)-1-piperazinyl]methyl]-9H-purine as a residue (compound 23).

Example 11

A mixture of 3.3 parts of 3-(2-ethoxyethyl)-2-[4-(1-piperazinyl)butyl]-3H-imidazo[4,5-b]pyridine, 2.9 parts of 2-(chloromethyl)-3-(2-ethoxyethyl)-3H-imidazo[4,5-b]pyridine, 1.2 parts of sodium carbonate and 22.5 parts of N,N-dimethylacetamide was stirred for 6 hours at 70° C. The reaction mixture was evaporated and the residue was extracted with dichloromethane. The extract was dried, filtered and evaporated. The residue was converted into the ethanedioate salt in 2-propanol. The salt was filtered off and crystallized from 2-propanol. The product was filtered off and dried, yielding 0.7 parts (6.8%) of 3-(2-ethoxyethyl)-2-[[4-[4-[3-(2-ethoxyethyl)-3H-imidazo-4,5-b]pyridin-2-yl]butyl]-1-piperazinyl]methyl]-3H-imidazo[4,5-b]pyridine ethanedioate(1:6); mp. 121.9° C. (compound 24).

Example 12

To a stirred solution of 8 parts of ethyl 4-[[3-[(5-methyl-2-furanyl)methyl]-3H-imidazo[4,5-b]pyridin-2-yl]methyl]-1-piperazinecarboxylate in 84 parts of 2-propanol were added 11.8 parts of potassium hydroxide. After stirring for 3 hours at reflux temperature, the reaction mixture was allowed to stand overnight at room temperature. The mixture was evaporated and the residue was taken up in water. The product was extracted with dichloromethane. The extract was washed with water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the (E)-2-butenedioate salt in 2-propanol. The salt was filtered off and dried, yielding 4.61 parts (40.3%) of 3-[(5-methyl-2-furanyl)methyl]-2-(1-piperazinylmethyl)-3H-imidazo[4,5-b]pyridine (E)-2-butenedioate(1:2); mp. 187.0° C. (compound 25).

In a similar manner there were also prepared:
3-(2-ethoxyethyl)-2-(1-piperazinylmethyl)-3H-imidazo[4,5-b]pyridine (E)-2-butenedioate(1:1); mp. 183.3° C. (compound 26);
3-[(3-methyl-2-furanyl)methyl]-2-(1-piperazinylmethyl)-3H-imidazo[4,5-b]pyridine (E)-2-butenedioate(1:1); mp. 170.9° C. (compound 27);
3-(2-ethoxyethyl)-2-(1-piperazinylmethyl)-3H-imidazo[4,5-b]pyridine; mp. 108.2° C. (compound 28);
3-(2-ethoxyethyl)-2-[2-(1-piperazinyl)ethyl]-3H-imidazo[4,5-b]pyridine (E)-2-butenedioate(1:2) monohydrate; mp. 166.1° C. (compound 29); and
3-(2-ethoxyethyl)-2-[(3-methyl-1-piperazinyl)methyl]-3H-imidazo[4,5-b]pyridine (E)-2-butenedioate(2:3); mp. 159.9° C. (compound 30).

Example 13

A mixture of 8.3 parts of 1-(2-ethoxyethyl)-2-[[4-(phenylmethyl)-1-piperazinyl]methyl]-1H-imidazo[4,5-b]pyridine and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol, saturated with ammonia, (90:10 by volume) as eluent. The pure fractions were collected and the eluent was evaporated, yielding 3.2 parts (46.1%) of 1-(2-ethoxyethyl)-2-(1-piperazinylmethyl)-1H-imidazo[4,5-b]pyridine as a residue (compound 31).

In a similar manner there were also prepared:
3-(2-ethoxyethyl)-2-[(hexahydro-1H-1,4-diazepin-1-yl)methyl]-3H-imidazo[4,5-b]pyridine (E)-2-butenedioate(1:2) 2-propanolate(2:1); mp. 145.5° C. (compound 32);
3-(2-ethoxyethyl)-2-[3-(1-piperazinyl)propyl]-3H-imidazo[4,5-b]pyridine (E)-2-butenedioate(1:2); mp. 160.7° C. (compound 33);
3-(2-ethoxyethyl)-2-[(2-methyl-1-piperazinyl)methyl]-3H-imidazo[4,5-b]piperidine (E)-2-butenedioate(2:3); mp. 169.6° C. (compound 34);
9-(2-ethoxyethyl)-8-(1-piperazinylmethyl)-9H-purine (E)-2-butenedioate(2:3); mp. 170.4° C. (compound 35);
3-(2-ethoxyethyl)-2-(1-piperazinylmethyl)-3H-imidazo[4,5-c]pyridine (E)-2-butenedioate(2:3); mp. 200.5° C. (compound 36); and
1-(2-ethoxyethyl)-2-(1-piperazinylmethyl)-1H-imidazo[4,5-c]pyridine (E)-2-butenedioate(2:3); mp. 169.7° C. (compound 37).

Example 14

A mixture of 2.7 parts of 3-(2-ethoxyethyl)-2-(1-piperazinylmethyl)-3H-imidazo[4,5-c]pyridine, 2.7 parts of 1-(2-bromoethyl)-4-ethyl-1,4-dihydro-5H-tetrazol-5-one, 1.3 parts of sodium carbonate and 72 parts of N,N-dimethylacetamide was stirred overnight at 70° C. The reaction mixture was poured into water and the product was extracted with dichloromethane. The extract was dried, filtered and evaporated. The residue was converted into the ethanedioate salt in 2-propanol. The salt was filtered off and dried, yielding 3.9 parts (64.0%) of 1-[2-[4-[[3-(2-ethoxyethyl)-3H-imidazo[4,5-b]pyridin-2-yl]methyl]-1-piperazinyl]ethyl]]-4-ethyl-1,4-dihydro-5H-tetrazol-5-one ethanedioate(1:2); mp. 170.9° C. (compound 38).

In a similar manner there were also prepared:

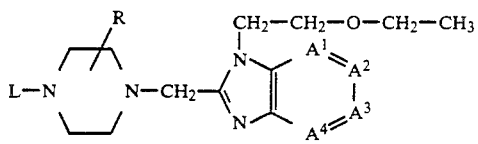

| Comp. No. | L | R | —$A^1$=$A^2$—$A^3$=$A^4$— | base/salt | mp. °C. |
|---|---|---|---|---|---|
| 39 | (4-methyl-1H-imidazol-5-yl)methyl- | H | —N=CH—CH=CH— | eth. (1:2) | 153.0 |
| 40 | 3-phenyl-2-propenyl- | H | —N=CH—CH=CH— | (E)-2-but. (1:2) | 166.5 |
| 41 | [benzodioxane-CH₂—] | H | —N=CH—CH=CH— | eth. (1:2) | 189.3 |
| 42 | 2-ethoxyethyl- | H | —N=CH—CH=CH— | eth. (1:2) | 166.2 |
| 43 | [coumarin-CH₂—CH₂—] | H | —N=CH—CH=CH— | base | 123.9 |
| 44 | H₃C—C(=O)—CH₂—CH₂—CH₂— | H | —N=CH—CH=CH— | eth. (1:2) | 185.9 |

-continued $$\underset{L-N}{\overset{R}{\bigcirc}}N-CH_2-\underset{\underset{A^4}{\parallel}}{\overset{CH_2-CH_2-O-CH_2-CH_3}{\underset{A^3}{\overset{A^1}{\underset{\parallel}{\overset{\parallel}{\bigcirc}}}}}}$$

| Comp. No. | L | R | —A¹=A²—A³=A⁴— | base/salt | mp. °C. |
|---|---|---|---|---|---|
| 45 | 5-methyl-7-oxo-5H-thiazolo[3,2-a]pyrimidin-6-yl-ethyl (thiazolo-pyrimidinone with CH₃ and CH₂—CH₂—) | 3-CH₃ | —N=CH—CH=CH— | (E)-2-but. (1:2) | 114.6 |
| 46 | 3-methyl-4-oxo-4H-pyrido[1,2-a]pyrimidin-2-yl (pyrido-pyrimidinone with CH₃ and CH₂—CH₂—) | 2-CH₃ | —N=CH—CH=CH— | (E)-2-but. (1:2) ½ H₂O | 146.0 |
| 47 | [2-(4-methoxyphenyl)-ethyl]- | H | —N=CH—CH=CH— | eth. (1:2) | 172.4 |
| 48 | thiazolo-pyrimidinone with CH₃ and CH₂—CH₂— | 2-CH₃ | —N=CH—CH=CH— | (E)-2-but. (1:2) | 141.9 |
| 49 | pyrido-pyrimidinone with CH₃ and CH₂—CH₂— | H | —CH=CH—CH=N— | (E)-2-but. (1:1) | 210.9 |
| 50 | pyrido-pyrimidinone with CH₃ and CH₂—CH₂— | 3-CH₃ | —N=CH—CH=CH— | (E)-2-but. (1:2) | 85.8 |
| 51 | thiazolo-pyrimidinone with CH₃ and CH₂—CH₂— | H | —N=CH—CH=CH— | (E)-2-but. (1:2) | 185.6 |
| 52 | thiazolo-pyrimidinone with CH₃ and CH₂—CH₂— | H | —CH=N—CH=CH— | (E)-2-but. (2:3) | 212.9 |
| 53 | pyrido-pyrimidinone with CH₃ and CH₂—CH₂— | H | —CH=N—CH=CH— | (E)-2-but. (2:3) | 215.9 |
| 54 | pyrido-pyrimidinone with CH₃ and CH₂—CH₂— | H | —CH=CH—N=CH— | (E)-2-but. (2:3) | 199.5 |

-continued

Structure: L-N(piperazine with R)-N-CH₂-[imidazole with N-CH₂-CH₂-O-CH₂-CH₃ and fused ring A¹=A²-A³=A⁴]

| Comp. No. | L | R | —A¹=A²—A³=A⁴— | base/salt | mp. °C. |
|---|---|---|---|---|---|
| 55 | thiazolo-pyrimidinone with CH₃, CH₂-CH₂- | H | —CH=CH—N=CH— | (E)-2-but. (2:3) | 190.3 |
| 56 | thiophene-2-yl-CH₂-CH₂- | H | —N=CH—CH=CH— | (E)-2-but. (2:3) | 183.5 |
| 57 | pyrido-pyrimidinone with CH₃, CH₂-CH₂- | H | —N=CH—N=CH— | (E)-2-but. (1:2) | 189.3 |
| 58 | theophylline-7-yl-CH₂-CH₂- | H | —N=CH—CH=CH— | 2 eth. (1:2) | 187.9 |
| 59 | quinazoline-2,4-dione-N-CH₂-CH₂- | H | —N=CH—CH=CH— | eth./H₂O | 221.9 |
| 60 | thiazolo-pyrimidinone with CH₃, CH₂-CH₂- | H | —N=CH—N=CH— | (E)-2-but. (1:2) | 164.3 |
| 61 | pyrido-pyrimidinone with CH₃, CH₂-CH₂- | H | —CH=N—CH=N— | | |
| 62 | thiazolo-pyrimidinone with CH₃, CH₂-CH₂- | H | —CH=N—CH=N— | | |
| 63 | phenyl-S-CH₂-CH₂- | H | —N=CH—CH=CH— | | |

-continued

| Comp. No. | L | R | —A¹=A²—A³=A⁴— | base/salt | mp. °C. |
|---|---|---|---|---|---|
| 64 | | H | —N=CH—CH=CH— | | |
| 65 | | H | —N=CH—CH=CH— | | |
| 66 | | H | —N=CH—CH=CH— | | |
| 67 | | H | —N=CH—CH=CH— | | |
| 68 | | H | —N=CH—CH=CH— | | |
| 69 | | H | —N=CH—CH=CH— | | |
| 70 | | H | —N=CH—CH=CH— | | |
| 71 | | H | —N=CH—CH=CH— | | |
| 72 | | H | —N=CH—CH=CH— | | |
| 73 | | H | —N=CH—CH=CH— | | |

(E)-2-but. = (E)-2-butenedioate
eth. = ethanedioate

Example 15

A mixture of 2.5 parts of 5-(2-chloroethyl)-4-methylthiazole, 2.8 parts of 3-(2-ethoxyethyl)-2-(1-piperazinylmethyl)-3H-imidazo[4,5-b]pyridine, 1.5 parts of N,N-diethylethanamine and 80 parts of N,N-dimethylacetamide was stirred over weekend at 70° C. The reaction mixture was evaporated and the residue was taken up in water. The product was extracted with dichloromethane. The extract was washed with a sodium carbonate solution, dried, filtered and evaporated. The residue was purified by column chromatography over silica gel using a mixture of dichloromethane and methanol (97:3 by volume) as eluent. The pure fractions were collected and the eluent was evaporated. The residue was converted into the ethanedioate salt in 2-propanol. The product was filtered off and dried, yielding 0.9 parts (15.1%) of 3-(2-ethoxyethyl)-2-[[4-[2-(4-methyl-5-thiazolyl)ethyl]-1-piperazinyl]methyl]-3H-imidazo[4,5-b]pyridine ethanedioate(1:2); mp. 189.5° C. (compound 74).

Example 16

A mixture of 5.3 parts of chloroacetonitrile, 14.4 parts of 3-(2-ethoxyethyl)-2-(1-piperazinylmethyl)-3H-imidazo[4,5-b]pyridine, 7.4 parts of sodium carbonate and 288 parts of N,N-dimethylformamide was stirred overnight at room temperature. The reaction mixture was stirred into water and the product was extracted with dichloromethane. The extract was dried, filtered and evaporated. The residue was purified by column chromatography over silica gel using a mixture of dichloromethane and methanol (95:5 by volume) as eluent. The pure fractions were collected and the eluent was evaporated. The residue was stirred in 2,2'-oxybispropane. The product was filtered off and dried, yielding 13 parts (79.2%) of 4-[[3-(2-ethoxyethyl)-3H-imidazo[4,5-b]pyridin-2-yl]methyl]-1-piperazineacetonitrile; mp. 80.7° C. (compound 75).

In a similar manner there were also prepared:

3-[2-[4-[[3-(2-ethoxyethyl)-3H-imidazo[4,5-b]pyridin-2-yl]methyl]-1-piperazinyl]ethyl]-2-methyl-4H-pyrido[1,2-a]pyrimidin-4-one (E)-2-butenedioate(1:1) 2-propanolate(2:1); mp. 187.8° C. (compound 76);

1-[3-[4-[[3-(2-ethoxyethyl)-3H-imidazo[4,5-b]pyridin-2-yl]methyl]-1piperazinyl]propyl]-1,3-dihydro-2H-benzimidazol-2-one ethanedioate(1:2); mp. 217.6° C. (compound 77);

4-[4-[[3-(2-ethoxyethyl)-3H-imidazo[4,5-b]pyridin-2-yl]methyl]-1-piperazinyl]-1-(4-fluorophenyl)-1-butanone ethanedioate(1:2); mp. 152.4° C. (compound 78);

3-(2-ethoxyethyl)-2-[[4-[3-(4-fluorophenoxy)propyl]-1-piperazinyl]methyl]-3H-imidazo[4,5-b]pyridine ethanedioate(1:2); mp. 160.5° C. (compound 79); and ethyl 4-[[3-(2-ethoxyethyl)-3H-imidazo[4,5-b]pyridin-2-yl]methyl]-1-piperazineacetate ethanedioate(1:2); mp. 166.8° C. (compound 80).

Example 17

A mixture of 2.7 parts of 6-(2-chloroethyl)-1,7-dimethyl-1H,5H-imidazo[1,2-a]pyrimidin-5-one, 2.9 parts of 3-(2-ethoxyethyl)-2-(1-piperazinylmethyl)-3H-imidazo[4,5-b]pyridine, 1.06 parts of sodium carbonate and 80 parts of 4-methyl-2-pentanone was stirred first for 44 hours at reflux temperature and then over weekend at room temperature. The reaction mixture was evaporated and the residue was taken up in water. The product was extracted with dichloromethane. The extract was washed with water, dried, filtered and evaporated. The residue was purified by column chromatography over silica gel using a mixture of trichloromethane and methanol (90:10 by volume) as eluent. The pure fractions were collected and the eluent was evaporated. The residue was converted into the (E)-2-butenedioate salt in 2-propanol. The salt was filtered off and dried, yielding 3.36 parts (47.3%) of 6-[2-[4-[[3-(2-ethoxyethyl)-3H-imidazo[4,5-b]-pyridin-2-yl]methyl]1-piperazinyl]ethyl]-1,7-dimethyl-1H,5H-imidazo[1,2-a]pyrimidin-5-one (E)-2-butenedioate(1:2); mp. 162.5° C. (compound 81).

In a similar manner there were also prepared:

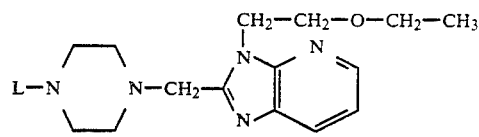

| Comp. No. | L | base/salt | mp. °C |
|---|---|---|---|
| 82 | 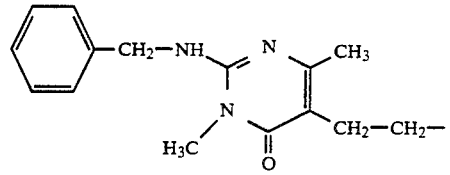 | eth. (2:5) | 120.7 |
| 83 | 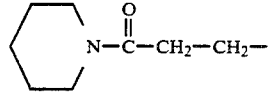 | (E)-2-but. (1:2) | 153.8 |

-continued
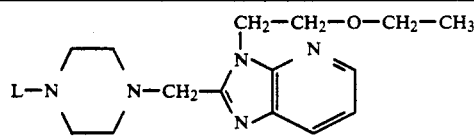
| Comp. No. | L | base/salt | mp. °C. |
|---|---|---|---|
| 84 | | 0.5 H₂O | 120.7 |
| 85 | | (E)-2-but (1:2) 2-propanolate (1:1) | 87.5 |
| 86 | | base | 169.6 |
| 87 | | | |
| 88 | | | |
| 89 | | | |
| 90 | | | |
| 91 | | | |
(E)-2-but. = (E)-2-butenedioate
eth. = ethanedioate

Example 18

A mixture of 1.4 parts of 3-bromo-1-propene, 2.8 parts of 3-(2-ethoxyethyl)-2-(1-piperazinylmethyl)-3H-imidazo[4,5-b]pyridine, 1.26 parts of sodium hydrogen carbonate and 64 pars of ethanol was stirred for 4 hours at reflux temperature. The reaction mixture was filtered over diatomaceous earth and the filtrate was evaporated. The residue was purified by column chromatography over silica gel using a mixture of dichloromethane and methanol (93:7 by volume) as eluent. The pure fractions were collected and the eluent was evaporated. The residue was converted into the (E)-2-butenedioate salt in 2-propanol. The salt was filtered off and dried, yielding 2 parts (39.7%) of 3-(2-ethoxyethyl)-2-[[4-(2-propenyl)-1-piperazinyl]methyl]-3H-imidazo[4,5-b]pyridine (E)-2-butenedioate(2:3); mp. 175.3° C. (compound 92).

In a similar manner there were also prepared:

4-[[3-(2-ethoxyethyl)-3H-imidazo[4,5-b]pyridin-2-yl]methyl]-N-(1-methylethyl)-1-piperazinepropanamide (E)-2-butenedioate(2:5); mp. 169.8° C. (compound 93);

3-(2-ethoxyethyl)-2-[[4-[2-(phenylsulfonyl)ethyl]-1-piperazinyl]methyl]-3H-imidazo[4,5-b]pyridine (E)-2-butenedioate(1:2); mp. 164.2° C. (compound 94); and 2,2'-[(1,4-piperazinediyl)bismethyl]bis[3-(2-ethoxyethyl)-3H-imidazo[4,5-b]pyridine (E)-2-butenedioate(1:2); mp. 219.1° C. (compound 95).

Example 19

A mixture of 4.15 parts of 2,4-dimethoxybenzaldehyde, 2.8 parts of 3-(2-ethoxyethyl)-2-(1-piperazinylmethyl)-3H-imidazo[4,5-b]pyridine, 2 parts of a solution of thiophene in methanol and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column chromatography over silica gel using a mixture of dichloromethane and methanol (95:5 by volume) as eluent. The pure fractions were collected and the eluent was evaporated. The residue was converted into the ethanedioate salt in 2-propanol. The product was filtered off and dried, yielding 4.38 parts (70.7%) of 2-[[4-[(2,4-dimethoxyphenyl)methyl]-1-piperazinyl]methyl]-3-(2-ethoxyethyl)-3H-imidazo[4,5-b]pyridine ethanedioate(1:2); mp. 173.4° C. (compound 96).

In a similar manner there were also prepared:

3-(2-ethoxyethyl)-2-[4-(4-methyl-1-piperazinyl)butyl]-3H-imidazo[4,5-b]pyridine (E)-2-butenedioate(1:2); mp. 186.0° C. (compound 97);

3-(2-ethoxyethyl)-2-[3-(4-methyl-1-piperazinyl)propyl]-3H-imidazo[4,5-b]pyridine (E)-2-butenedioate(1:3); mp. 183.7° C. (compound 98);

3-(2-ethoxyethyl)-2-[[4-(1-methylethyl)-1-piperazinyl]methyl]-3H-imidazo-[4,5-b]pyridine ethanedioate(1:2); mp. 167.7° C. (compound 99);

2-[(2,4-dimethyl-1-piperazinyl)methyl]-3-(2-ethoxyethyl)-3H-imidazo[4,5-b]pyridine (E)-2-butenedioate(2:3); mp. 155.5° C. (compound 100);

2-[(3,4-dimethyl-1-piperazinyl)methyl]-3-(2-ethoxyethyl)-3H-imidazo[4,5-b]pyridine (E)-2-butenedioate(2:3); mp. 157.1° C. (compound 101);

3-(2-ethoxyethyl)-2-[(4-ethyl-1-piperazinyl)methyl]-3H-imidazo[4,5-b]pyridine (E)-2-butenedioate(2:3); mp. 185.0° C. (compound 102);

3-(2-ethoxyethyl)-2-[[4-[(3,4,5-trimethoxyphenyl)methyl]-1-piperazinyl]methyl]-3H-imidazo-[4,5-b]pyridine ethanedioate(1:2); mp. 183.1° C. (compound 103); and 9-(2-ethoxyethyl)-8-[(4-methyl-1-piperazinyl))methyl]-9H-purine; mp. 69.7° C. (compound 104).

Example 20

A mixture of 1.26 parts of 2-chloropyrimidine, 3.6 parts of 4-[[3-(2-ethoxyethyl)-3H-imidazo[4,5-b]pyridin-2-yl]methyl]-1-piperazineethanamine, 1.1 parts of sodium hydrogen carbonate and 64 parts of ethanol was stirred overnight at reflux temperature. The reaction mixture was evaporated and the residue was taken up in water. The product was extracted with dichloromethane. The extract was dried, filtered and evaporated. The residue was purified by column chromatography over silica gel using a mixture of dichloromethane and methanol (93:7 by volume) as eluent. The pure fractions were collected and the eluent was evaporated. The residue was converted into the ethanedioate salt in 2-propanol. The product was filtered off and dried, yielding 3.8 parts (64.3%) of N-[2-[-4-[[3-(2-ethoxyethyl)-3H-imidazo[4,5-b]pyridin-2-yl]methyl]-1-piperazinyl]ethyl]-2-pyrimidinamine ethanedioate(1:2); mp. 175.3° C. (compound 105).

In a similar manner there is also prepared: N-[2-[-4-[[3-(2-ethoxyethyl)-3H-imidazo[4,5-b]pyridin-2-y]methyl]1-piperazinyl]ethyl)-5-methyl-1,3,4-thiadiazol-2-amine (compound 106).

Example 21

To a stirred mixture of 5.2 parts of 4-[[3-(2-ethoxyethyl)-3H-imidazo[4,5-b)pyridin-2-yl]methyl]-1-piperazineethanol and 94 parts of N,N-dimethylformamide were added portionwise 0.82 parts of a sodium hydride dispersion 50% under nitrogen atmosphere. After cooling, 1.95 parts of 2-chloropyrimidine were added and the mixture was stirred overnight at room temperature. The reaction mixture was evaporated and the residue was taken up in water. The product was extracted with dichloromethane. The extract was dried, filtered and evaporated. The residue was purified by column chromatography over silica gel using a mixture of trichloromethane and methanol (90:10 by volume) as eluent. The pure fractions were collected and the eluent was evaporated. The residue was converted into the (E)-2-butenedioate salt in 2-propanol. The product was filtered off and dried, yielding 5.42 parts (54.0%) of 3-(2-ethoxyethyl)-2-[[4-[2-(2-pyrimidinyloxy)ethyl]-1-piperazinyl]methyl]-3H-imidazo[4,5-b]pyridine (E)-2-butendioate(1:2); mp. 155.3° C. (compound 107).

In a similar manner there are also prepared:

3-(2-ethoxyethyl)-2-[[4-[2-[(thiazolo[5,4-b]pyridin-2-yl)thio]ethyl]-1-piperazinyl]methyl]-3H-imidazo[4,5-b]pyridine (compound 108); and 3-(2-ethoxyethyl)-2-[[4-[2-[(thiazolo[5,4-b]pyridin-2-yl)oxy]ethyl]-1-piperazinyl]methyl]-3H-imidazo[4,5-b]pyridine (compound 109).

Example 22

To a stirred mixture of 1.12 parts of 3-furancarboxylic acid, 2 parts of N,N-diethylethanamine and 195 parts of dichloromethane were added 2.6 parts of 2-chloro-1-methylpyridinium iodide. After stirring for 1 hour at room temperature, 3.6 parts of 4-[[3-(2-ethoxyethyl)-3H-imidazo[4,5-b]pyridin-2-yl]methyl]-1-piperazineethanamine and the mixture was stirred for 6 hours at room temperature. The reaction mixture was poured into water and the layers were separated. The organic layer was dried, filtered and evaporated. The residue was purified by column chromatography over silica gel using a mixture of dichloromethane and methanol, saturated with ammonia (95:5 by volume) as eluent. The pure fractions were collected and the eluent was evaporated. The residue was converted into the ethanedioate salt in 2-propanol. The salt was filtered off and crystallized from acetonitrile. The product was filtered off and dried, yielding 2.4 parts (39.6%) of N-[2-[4-[[3-(2-ethoxyethyl)-3H-imidazo[4,5-b]pyridin-2-yl]methyl]-1-piperazinyl]ethyl]-3-furancarboxamide ethanedioate(1:2); 132.2° C. (compound 110).

In a similar manner there were also prepared:

N-[2-[4-[[3-(2-ethoxyethyl)-3H-imidazo[4,5-b]pyridin-2-yl]methyl]-1-piperazinyl]ethyl]-1-methyl-1H-pyrrole-2-carboxamide; mp. 132.6° C. (compound 111);

N-[2-[4-[[3-(2-ethoxyethyl)-3H-imidazo[4,5-b]pyridin-2-yl]methyl]-1-piperazinyl]ethyl]-4-nitrobenzamide; mp. 180.7C° C. (compound 112); and N-[2-[4-[[3-(2-ethoxyethyl)-3H-imidazo[4,5-b]pyridin-2-yl]methyl]-1-piperazinyl]ethyl]-1-methyl-1H-indole-2-carboxamide ethanedioate(1:2) (compound 113).

In a similar manner there are also prepared:

2-amino-N-[2-[4-[[3-(2-ethoxyethyl)-3H-imidazo[4,5-b]pyridin-2-yl]methyl]-1-piperazinyl]ethyl]benzamide (compound 114); and 3-amino-N-[2-[4-[[3-(2-ethoxyethyl)-3H-imidazo[4,5-b]pyridin-2-yl]methyl]-1-piperazinyl]ethyl]-2-pyrazinecarboxamide (compound 115).

Example 23

A mixture of 0.7 parts of isocyanatoethane, 3.6 parts 4-[[3-(2-ethoxyethyl)-3H-imidazo[4,5-b]pyridin-2-yl]methyl]-1-piperazineethanamine and 135 parts of tetrahydrofuran was stirred over weekend at room temperature. The reaction mixture was evaporated and the residue was taken up in dichloromethane. The extract was washed with water, dried, filtered and evaporated. The residue was converted into the ethanedioate salt in 2-propanol. The product was filtered off and dried, yielding 2.2 parts (35.8%) of N-[2-[4-[[3-(2-ethoxyethyl)-3H-imidazo[4,5-b]pyridin-2-yl]methyl]-1-piperazinyl]ethyl]N'-methylurea ethanedioate(2:5); mp. 144.5° C. (compound 116).

In a similar manner there was also prepared: N-[2-[4-[[3-(2-ethoxyethyl)-3H-imidazo[4,5-b]pyridin-2-yl]methyl]-1-piperazinyl]ethyl]-N'-methylthiourea ethanedioate(1:2); mp. 119.7° C. (compound 117).

Example 24

A mixture of 1.65 parts of 2-(phenoxymethyl)oxirane, 8.9 parts of 3-(2-ethoxyethyl)-2-(1-piperazinylmethyl)-3H-imidazo[4,5-b]pyridine and 40 parts of 2-propanol was stirred for 20 hours at reflux temperature. The reaction mixture was evaporated and the residue was purified by column chromatography over silica gel using a mixture of trichloromethane and methanol (95:5 by volume) as eluent. The pure fractions were collected and the eluent was evaporated. The residue was crystallized from 2,2'-oxybispropane. The product was filtered off and dried, yielding 1.36 parts (31.0%) of 4-[[3-(2-ethoxyethyl)-3H-imidazo[4,5-b]pyridin-2-yl]methyl]-α-(phenoxymethyl)-1-piperazineethanol; mp. 102.5° C. (compound 118).

In a similar manner there were also prepared: 4-[[3-(2-ethoxyethyl)-3H-imidazo[4,5-b]pyridin-2-yl]methyl]-1-piperazineethanol ethanedioate(1:2); mp. 152.0° C. (compound 119).

Example 25

A mixture of 2.7 parts of 3-(2-ethoxyethyl)-2-(1-piperazinylmethyl)-3H-imidazo[4,5-b]pyridine, 3 parts of 2-ethenylpyridine and 80 parts of 1-butanol was stirred overnight at 125° C. The reaction mixture was evaporated and the residue was poured into water. The product was extracted with dichloromethane. The extract was dried, filtered and evaporated. The residue was purified by column chromatography over silica gel using a mixture of trichloromethane and methanol (90:10 by volume) as eluent. The pure fractions were collected and the eluent was evaporated. The residue was converted into the (E)-2-butenedioate salt in 2-propanol. The salt was filtered off and dried, yielding 3.3 parts (48.2%) of 3-(2-ethoxyethyl)-2-[[4-[2-(2-pyridinyl)ethyl]-1-piperazinyl]methyl]-3H-imidazo[4,5-b]pyridine (E)-2-butenedioate(2:5); mp. 162.1° C. (compound 120).

Example 26 a) To a stirred and cooled (−10° C.) mixture of 18 parts of carbon disulfide, 7.22 parts of N,N'-methanetetraylbis[cyclohexanamine] and 135 parts of tetrahydrofuran was added dropwise a solution of 12.9 parts of 4-[[3-(2-ethoxyethyl)-3H-imidazo[4,5-b]pyridin-2-yl]methyl]-1-piperazineethanamine in tetrahydrofuran. Upon complete addition, the temperature was allowed to reach room temperature. After stirring for 1 hour at room temperature, the mixture was evaporated, yielding 13.1 parts (100%) of 3-(2-ethoxyethyl)-2-[[4-(2-isothiocyanatoethyl)-1-piperazinyl]methyl]-3H-imidazo[4,5-b]pyridine as a residue (compound 121)

b) A mixture of 3.8 parts of 3,4-pyridinediamine, 13.1 parts of 3-(2-ethoxyethyl)-2-[[4-(2-isothiocyanatoethyl)-1-piperazinyl]methyl]-3H-imidazo[4,5-b]-pyridine and 135 parts of tetrahydrofuran was stirred overnight at reflux temperature. The whole was evaporated, yielding 16.9 pars (100%) of N-(4-amino-3-pyridinyl)-N'-[2-[4-[[3-(2-ethoxyethyl)-3H-imidazo[4,5-b]pyridin-2-yl]methyl]-1-piperazinyl]ethyl]thiourea as a residue (compound 122).

c) A mixture of 16.9 parts of N-(4-amino-3-pyridinyl)-N'-[2-[4-[[3-(2-ethoxyethyl)-3H-imidazo[4,5-b]pyridin-2-yl]methyl]-1-piperazinyl]ethyl]thiourea, 11.4 parts of mercury(II)oxide, 0.1 parts of sulfur and 135 parts of tetrahydrofuran was stirred for 3 hours at reflux temperature. The reaction mixture was filtered while hot over diatomaceous earth and the filtrate was evaporated. The residue was purified by column chromatography over silica gel using a mixture of dichloromethane and methanol, saturated with ammonia, (90:10 by volume) as eluent. The pure fractions were collected and the eluent was evaporated. The residue was stirred in 2,2'-oxybispropane. The product was filtered off and dried, yielding 4.73 parts (30.0%) of N-[2-[4-[[3-(2-ethoxyethyl)-3H-imidazo[4,5-b]pyridin-2-yl]methyl]-1-piperazinyl]ethyl]-1H-imidazo[4,5-c]pyridin-2-amine; mp. 124.5° C. (compound 123).

Example 27

A mixture of 14 parts of N-(2,2-dimethoxyethyl)-N'-[2-[4-[[3-(2-ethoxyethyl)-3H-imidazo[4,5-b]pyridin-2-yl]methyl]-1-piperazinyl]ethyl]guanidine monohydroiodide and 140 parts of a hydrochloric acid solution 1N was stirred for 48 hours at room temperature. The mixture was treated with a sodium hydroxide solution and the product was extracted with dichloromethane. The extract was dried, filtered and evaporated. The residue was purified by column chromatography over silica gel using a mixture of dichloromethane and methanol, saturated with ammonia (90:10 by volume) as eluent. The pure fractions were collected and the eluent was evaporated. The residue was refluxed with methylbenzene and 4-methylbenzenesulfonic acid. The whole was evaporated and the residue was taken up in water and dichloromethane. The mixture was treated with a sodium hydroxide solution and the layers were separated. The organic layer was dried, filtered and evaporated. The residue was further purified by column chromatography over silica gel using a mixture of dichloromethane and methanol (90:10 by volume) as eluent. The pure fractions were collected and the eluent was evaporated. The residue was converted into the ethanedioate salt in 2-propanol. The salt was filtered off and dried, yielding 0.65 parts (3.7%) of 4-[[3-(2-ethoxyethyl)-3H-imidazo[4,5-b]pyridin-2-yl]methyl]-N-(1H-imidazol-2-yl)-1-piperazineethanamine ethanedioate(1:2); mp. 170.5° C. (compound 124).

Example 28

To a stirred solution of 2.5 parts of 2-[(4-methyl-1-piperazinyl)methyl]-3H-imidazo[4,5-b]pyridine-3-ethanol in 22.5 parts of N,N-dimethylformamide were added portionwise 0.48 parts of a sodium hydride dispersion 50%. Upon complete addition, stirring was continued first for 1 hour at room temperature and then for 1 hour at 30° C. After cooling, 0.723 parts of 3-chloro-1-propenyl were added (exothermic reaction). The reaction mixture was stirred for 3 hours at room temperature. The whole was poured into water and the product was extracted three times with methylbenzene and twice with dichloromethane. The combined extracts were dried, filtered and evaporated. The residue was purified by column chromatography over silica gel using a mixture of trichloromethane and methanol (95:5 by volume) as eluent. The pure fractions were collected and the eluent was evaporated. The residue was crystallized from 2,2'oxybispropane. The product was filtered off and dried, yielding 1.42 parts (50.3%) of 2-[(4-methyl-1-piperazinyl)methyl]-3-[2-(2-propynyloxy)ethyl]-3H-imidazo[4,5-b]pyridine; mp. 117.3° C. (compound 125).

In a similar manner there was also prepared: 2-[(4-methyl-1-piperazinyl)methyl]-3-[2-(2-propenyloxy)ethyl]-3H-imidazo[4,5-b]pyridine (E)-2-butenedioate(1:2); mp. 159.0° C. (compound 126).

Example 29

A mixture of 6.3 parts of ethyl 4-[[3-(2-ethoxyethyl)-3H-imidazo[4,5-b]pyridin-2-yl]methyl]-1-piperazineacetamide, 17 parts of a sodium hydroxide solution 1N, 150 parts of water and 16 parts of ethanol was stirred overnight at room temperature. The reaction mixture was evaporated and the residue was taken up in water. The aqueous layer was washed with dichloromethane and a small amount of a hydrochloric acid solution 1N was added. The aqueous layer was evaporated and the residue was purified by column chromatography over silica gel using a mixture of dichloromethane and methanol, saturated with ammonia (75:25 by volume) as eluent. The second fraction was collected and the eluent was evaporated. The residue was stirred in 2-propanone. The precipitate was filtered off and the filtrate was acidified with a hydrochloric acid solution. The precipitated product was filtered off and dried in vacuo, yielding 0.8 parts (10.3%) of 4-[[3-(2-ethoxyethyl)-3H-imidazo-[4,5-b] pyridin-2-yl]methyl]-1-piperazineacetic acid trihydrochloride: mp. 181.4° C. (compound 127).

Example 30

A mixture of 41.8 parts of 4-[[3-(2-ethoxyethyl)-3H-imidazo-[4,5-b]pyridin-2-yl]methyl)-1-piperazineacetonitrile and 1100 parts of methanol, saturated with ammonia was hydrogenated at normal pressure and at room temperature with 20 parts of Raney nickel catalyst. After the calculated amount of hydrogen was taken up, the catalyst was filtered off and the filtrate was evaporated. The residue was converted into the (E)-2-butenedioate salt in 2-propanol. The salt was filtered off and crystallized from a mixture of acetonitrile and 2-propanol. The product was filtered off and dried, yielding 37.4 parts (52.1%) of 4-[[3-(2-ethoxyethyl)-3H-imidazo[4,5-b]pyridin-2-yl]methyl]-1-piperazineethanamine; mp. 159.8° C. (compound 128).

Example 31

A mixture of 16.7 parts of 2-[(4-methyl-1-piperazinyl)methyl]-3-[2-(phenylmethoxy)ethyl]-3H-imidazo[4,5-b]pyridine and 200 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from 2,2'-oxybispropane. The product was filtered off and dried, yielding 5.84 parts (46.1%) of 2-[(4-methyl-1-piperazinyl)methyl]-3H-imidazo[4,5-b]pyridine-3-ethanol; mp. 89.5° C. (compound 129).

C. Pharmacological Examples

The useful antihistaminic properties of the compounds of formula (I) are demonstrated in the following test procedure.

Example 32

Protection of rats from compound 48/80-induced lethality

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240-260 g were used in the experiment. After overnight starvation the rats were transferred to conditioned laboratories (temp.=21°±1° C., relative humidity=65±5%). The rats were treated subcutaneously or orally with a test compound or with the solvent (NaCl solution, 0.9%). One hour after treatment there was injected intraveneously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration. The $ED_{50}$-values of the compounds of formula (I) are listed in Table 1. Said $ED_{50}$-values are the values in mg/kg body weight at which the tested compounds protect 50% of the tested animals against compound 48/80-induced lethality.

TABLE 1

| Compound No. | compound 48/80 lethality test in rats-$ED_{50}$ in mg/kg body weight |
|---|---|
| 14 | 0.01 |
| 17 | 0.04 |
| 42 | 0.02 |
| 44 | 0.005 |
| 46 | 0.02 |
| 47 | 0.02 |
| 74 | 0.01 |
| 76 | 0.02 |
| 77 | 0.02 |
| 79 | 0.02 |
| 93 | 0.01 |
| 105 | 0.01 |
| 110 | 0.01 |
| 111 | 0.02 |
| 120 | 0.005 |
| 125 | 0.02 |
| 126 | 0.02 |

D) Composition Examples

The following formulations exemplify typical pharmaceutical compositions in dosage unit form suitable for systemic administration to animal and human subjects in accordance with the present invention.

"Active ingredient" (A.I.) as used throughout these examples relates to a compound of formula (I), a pharmaceutically acceptable acid addition salt or a stereochemically isomeric form thereof.

Example 33

Oral Drops

500 Parts of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 parts of sodium saccharin in 2.5 l of purified water and while stirring there were added 2.5 l of cocoa flavor and polyethylene glycol q.s. to a volume of 50 l, providing an oral drop solution comprising 0.01 parts of the A.I. per ml. The resulting solution was filled into suitable containers.

Example 34

Oral Solution

9 Parts of methyl 4-hydroxybenzoate and 1 part of propyl 4-hydroxybenzoate were dissolved in 4 l of boiling purified water. In 3 l of this solution were dissolved first 10 parts of 2,3-dihydroxybutanedioic acid and thereafter 20 parts of the A.I. The latter solution was combined with the remaining part of the former solution and 12 l 1,2,3-propanetriol and 3 l of sorbitol 70% solution were added thereto. 40 Parts of sodium saccharin were dissolved in 0.5 l of water and 2 ml of raspberry and 2 ml of gooseberry essence were added. The latter solution was combined with the former, water was added q.s. to a volume of 20 l providing an oral solution comprising 0.005 parts of the A.I. per teaspoonful (5 ml). The resulting solution was filled in suitable containers.

Example 35

Capsules

20 Parts of the A.I., 6 parts sodium lauryl sulfate, 56 parts starch, 56 parts lactose, 0.8 parts colloidal silicon dioxide, and 1.2 parts magnesium stearate were vigorously stirred together. The resulting mixture was subsequently filled into 1000 suitable hardened gelatin capsules, each comprising 0.02 parts of the A.I..

Example 36

Film-Coated Tablets

Preparation of tablet core

A mixture of 100 parts of the A.I., 570 parts lactose and 200 parts starch was mixed well and thereafter humidified with a solution of 5 parts sodium dodecyl sulfate and 10 parts polyvinylpyrrolidone (Kollidon-K 90 ®) in about 200 ml of water. The wet powder mixture was sieved, dried and sieved again. Then there was added 100 parts microcrystalline cellulose (Avicel ®) and 15 parts hydrogenated vegetable oil (Sterotex ®). The whole was mixed well and compressed into tablets, giving 10.000 tablets, each comprising 0.01 parts of the active ingredient.

Coating

To a solution of 10 parts methyl cellulose (Methocel 60 HG ®) in 75 ml of denaturated ethanol there was added a solution of 5 parts of ethyl cellulose (Ethocel 22 cps ®) in 150 ml of dichloromethane. Then there were added 75 ml of dichloromethane and 2.5 ml 1,2,3-propanetriol. 10 Parts of polyethylene glycol was molten and dissolved in 75 ml of dichloromethane. The latter solution was added to the former and then there were added 2.5 parts of magnesium octadecanoate, 5 parts of polyvinylpyrrolidone and 30 ml of concentrated color suspension (Opaspray K-1-2109 ®) and the whole was homogenated. The tablet cores were coated with the thus obtained mixture in a coating apparatus.

Example 37

Injectable Solution 1.8 Parts methyl 4-hydroxybenzoate and 0 2 parts propyl 4-hydroxybenzoate were dissolved in about 0.5 l of boiling water for injection. After cooling to about 50° C. there were added while stirring 4 parts lactic acid, 0.05 parts propylene glycol and 4 parts of the A.I. The solution was cooled to room temperature and supplemented with water for injection q.s. ad 1 l volume, giving a solution of 0.004 parts A.I. per ml. The solution was sterilized by filtration (U.S.P. XVII p. 811) and filled in sterile containers.

Example 38

Suppositories

3 Parts A.I. was dissolved in a solution of 3 parts 2,3-dihydroxybutanedioic acid in 25 ml polyethylene glycol 400. 12 Parts surfactant (SPAN ®) and triglycerids (Witepsol 555 ®) q.s. ad 300 parts were molten together. The latter mixture was mixed well with the former solution. The thus obtained mixture was poured into moulds at a temperature of 37°~38° C. to form 100 suppositories each containing 0.03 parts of the active ingredient.

We claim:

1. A method of treating allergic diseases in warm-blooded animals suffering from the same, which method comprises the systemic administration to warm blooded animals of an effective anti-allergic amount of a compound of the formula:

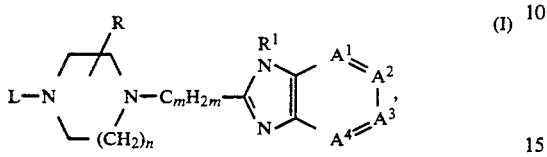

a pharmaceutically acceptable acid addition salt or a stereochemically isomeric form thereof, wherein:

—$A^1$=$A^2$—$A^3$=$A^4$— represents a bivalent radical of the formula:

—N=CH—N=CH— (a-5) or;

—CH=N—CH=N— (a-6), wherein one or two hydrogen atoms in said radicals (a-5) and (a-6) may, each independently from each other, be replaced by halo, $C_{1-6}$alkyl, $C_{1-6}$alkyloxy, trifluoromethyl, or hydroxy;

R represents hydrogen or $C_{1-6}$alkyl;

$R^1$ represents hydrogen, $C_{1-10}$alkyl, $C_{3-6}$cycloalkyl, $Ar^1$, $C_{1-6}$alkyl substituted with one or two $Ar^1$ radicals, or a radical of the formula —Alk—G—$R^2$, wherein:

$Ar^1$ represents phenyl; phenyl substituted with 1, 2 or 3 substitutents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl; thienyl; halothienyl; furanyl; $C_{1-6}$alkyl substituted furanyl; pyridinyl; pyrimidinyl; pyrazinyl; thiazolyl; imidazolyl; or imidazolyl substituted with $C_{1-6}$alkyl;

Alk represents $C_{1-6}$alkanediyl;

G represents O, S, or $NR^3$, wherein $R^3$ represents hydrogen, $C_{1-6}$alkyl, $C_{1-6}$alkylcarbonyl, $C_{1-6}$alkyloxycarbonyl, or $Ar^2$—$C_{1-6}$alkyl;

$Ar^2$ represents phenyl or phenyl substituted with 1, 2, or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl; and $R^2$ represents hydrogen; $C_{2-6}$alkenyl; $C_{2-6}$alkenyl substituted with $Ar^2$; $C_{3-6}$alkynyl; $Ar^1$; $C_{1-6}$alkyl; or $C_{1-6}$alkyl substituted with $Ar^1$, hydroxy, $C_{1-6}$alkyloxy, carboxyl, $C_{1-6}$alkyloxycarbonyl, $Ar^2$-oxycarbonyl, or $Ar^2$—$C_{1-6}$alkyloxycarbonyl, wherein $Ar^1$ and $Ar^2$ are as defined above;

m represents a number having a value of from 1 to 4;

n represents a number having a value of from 1 to 2; and

L represents hydrogen, $C_{1-6}$alkylcarbonyl, $C_{1-6}$alkylsulfonyl, $C_{1-6}$alkyloxycarbonyl, $Ar^2$—$C_{1-6}$alkyloxycarbonyl, $Ar^2$-carbonyl, $Ar^2$-sulfonyl, $C_{3-6}$cycloalkyl, $C_{2-6}$alkenyl, $C_{2-6}$alkenyl substituted with $Ar^2$, $C_{1-12}$alkyl, wherein $Ar^2$ is as defined above, or L represents a radical of the formula:

—Alk—$R^4$ (b-1);

—Alk—Y—$R^5$ (b-2); or

—Alk—$Z^1$—(C=X)—$Z^2$—$R^6$ (b-3)

wherein:

Alk is as defined above;

Y represents O, S, $NR^8$, wherein $R^8$ represents hydrogen $C_{1-6}$alkyl, $C_{1-6}$alkylcarbonyl, or $Ar^1$-carbonyl, wherein $Ar^1$ is as defined above;

$Z^1$ and $Z^2$ each independently represent O, S, $NR^9$, or a direct bond, wherein $R^9$ represents hydrogen or $C_{1-6}$alkyl;

X represents O, S, or $NR^{10}$, wherein $R^{10}$ represents hydrogen, $C_{1-6}$alkyl, or cyano;

$R^4$ represents Het, $Ar^2$, cyano, isocyanato, isothiocyanato, $Ar^2$-sulfonyl, or halo, wherein $Ar^2$ is as defined above;

$R^5$ represents hydrogen, Het, $Ar^2$, $C_{1-6}$alkyl, or $C_{1-6}$alkyl substituted with halo or $Ar^2$, wherein $Ar^2$ is as defined above; and $R^6$ represents hydrogen, Het, $Ar^2$, $C_{1-6}$alkyl, or $C_{1-6}$alkyl substituted with halo or $Ar^2$, wherein $Ar^2$ is as defined above; wherein Het represents:

(i) an optionally substituted five- or six-membered heterocyclic ring containining 1, 2, 3, or 4 heteroatoms selected from the group consisting of oxygen, sulfur, and nitrogen, provided that no more than two oxygens or sulfurs are present; or (ii) an optionally substituted five- or six-membered heterocyclic ring containing 1 or 2 heteroatoms selected from the group consisting of oxygen, sulfur, and nitrogen, being fused with an optionally substituted five- or six-membered ring through two ring carbon atoms or one ring carbon and one ring nitrogen atom, containing in the remainder of the fused ring only carbon atoms; or (iii) an optionally substituted five- or six-membered heterocyclic ring containing 1 or 2 heteroatoms selected from the group consisting of oxygen, sulfur, and nitrogen, being fused with an optionally substituted five- or six-membered heterocyclic ring through two ring carbon atoms or one ring carbon and one ring nitrogen atom, containing in the remainder of the fused ring 1 or 2 heteroatoms selected from the group consisting of oxygen, sulfur and nitrogen; wherein:

Het may optionally be substituted with up to 4 substituents when Het is a monocyclic ring system, and wherein Het may optionally be substituted with up to 5 substituents when Het is a bicyclic ring system, said substitutents of Het being selected from the group consisting of a bivalent radical =X; halo; isocyanato; isothiocyanato; nitro; cyano; trifluoromethyl; a radical of formula —A; a radical of formula —Y—A; or a radical of formula —$Z^1$—C(=X)—$Z^2$—A; wherein =X is as defined above;

A represents hydrogen, $Ar^2$, or $C_{1-6}$alkyl being optionally substituted with $Ar^2$, $C_{1-}$ ₆alkyloxy, Ar²—0, hydroxy, or C₁₋₆alkyloxycarbonyl; and Y, Z¹, and Z² each have the meaning as defined above;

provided that when in the radical —Z¹—C(=X)—Z²—A, A is hydrogen and Z¹ is NR⁹, O, or X, then Z² is other than O or S.

2. The method of claim 1 wherein $R^4$, $R^5$, and $R^6$ represent Het.

3. The method of claim 1 wherein:

$R^4$ represents $Ar^2$, cyano, isocyanato, isothiocyanato, $Ar^2$-sulfonyl, or halo;

$R^5$ represents hydrogen, $Ar^2$, $C_{1-6}$alkyl, or $C_{1-6}$alkyl substituted with halo or $Ar^2$; and $R^6$ represents hydrogen, $Ar^2$, $C_{1-6}$alkyl, or $C_{1-6}$alkyl substituted with halo or $Ar^2$.

4. The method of claim 1 wherein $R^1$ represents $C_{1-6}$alkyl substituted with $Ar^1$, or wherein $R^1$ represents —Alk—O—$R^2$ wherein $R^2$ represents hydrogen, $C_{1-6}$alkyl, $C_{2-6}$alkenyl, $C_{3-6}$alkynyl, or $Ar^1$.

5. The method of claim 4 wherein R is hydrogen, m is 1, n is 1, and L is hydrogen, $C_{1-6}$alkyl, or a radical of formula (b-1), (b-2), or (b-3).

6. The method of claim 5 wherein $R^4$ is $Ar^2$ or Het, $R^5$ and $R^6$ are $C_{1-4}$alkyl, X is O or S, and $Z^1$ and $Z^2$ are each independently NH or a direct bond.

7. The method of claim 6 wherein $R^1$ is an ethoxyethyl group.

8. A compound of the formula:

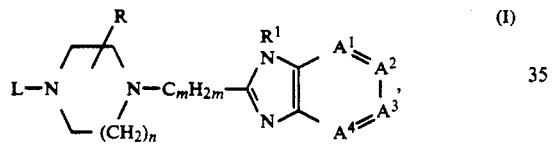

a pharmaceutically acceptable acid addition salt or a stereochemically isomeric form thereof, wherein:

—A¹=A²—A³=A⁴— represents a bivalent radical of the formula:

—N=CH—N=CH—    (a-5) or;

—CH=N—CH=N—    (a-6), wherein one or two hydrogen atoms in said radicals (a-5) and (a-6) may, each independently from each other, be replaced by halo, $C_{1-6}$alkyl, $C_{1-6}$alkyloxy, trifluoromethyl, or hydroxy;

R represents hydrogen or $C_{1-6}$alkyl;

$R^1$ represents hydrogen, $C_{1-10}$alkyl, $C_{3-6}$cycloalkyl, $Ar^1$, $C_{1-6}$alkyl substituted with one or two $Ar^1$ radicals, or a radical of the formula —Alk—G—$R^2$, wherein:

$Ar^1$ represents phenyl; phenyl substituted with 1, 2, or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl; thienyl; halothienyl; furanyl; $C_{1-6}$alkyl substituted furanyl; pyridinyl; pyrimidinyl; pyrazinyl; thiazolyl; imidazolyl; or imidazolyl substituted with $C_{1-6}$alkyl;

Alk represents $C_{1-6}$alkanediyl;

G represents O, S, or $NR^3$, wherein $R^3$ represents hydrogen, $C_{1-6}$alkyl, $C_{1-6}$alkylcarbonyl, $C_{1-6}$alkyloxycarbonyl, or $Ar^2$—$C_{1-6}$alkyl;

$Ar^2$ represents phenyl or phenyl substituted with 1, 2, or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl; and $R^2$ represents hydrogen; $C_{2-6}$alkenyl; $C_{2-6}$alkenyl substituted with $Ar^2$; $C_{3-6}$alkynyl; $Ar^1$; $C_{1-6}$alkyl; or $C_{1-6}$alkyl substituted with $Ar^1$, hydroxy, $C_{1-6}$alkyloxy, carboxyl, $C_{1-6}$alkyloxycarbonyl, $Ar^2$-oxycarbonyl, or $Ar^2$—$C_{1-6}$alkyloxycarbonyl, wherein $Ar^1$ and $Ar^2$ are as defined above;

m represents a number having a value of from 1 to 4;

n represents a number having a value of from 1 to 2; and

L represents hydrogen, $C_{1-6}$alkylcarbonyl, $C_{1-6}$alkylsulfonyl, $C_{1-6}$alkyloxycarbonyl, $Ar^2$—$C_{1-6}$alkyloxycarbonyl, $Ar^2$-carbonyl, $Ar^2$-sulfonyl, $C_{3-6}$cycloalkyl, $C_{2-6}$alkenyl, $C_{2-6}$alkenyl substituted with $Ar^2$, $C_{1-12}$alkyl, wherein $Ar^2$ is as defined above, or L represents a radical of the formula:

 (b-1)

 (b-2); or

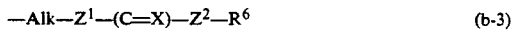 (b-3)

wherein:

Alk is as defined above;

Y represents O, S, $NR^8$, wherein $R^8$ represents hydrogen, $C_{1-6}$alkyl, $C_{1-6}$alkylcarbonyl, or $Ar^1$-carbonyl, wherein $Ar^1$ is as defined above;

$Z^1$ and $Z^2$ each independently represent O, S, $NR^9$, or a direct bond, wherein $R^9$ represents hydrogen or $C_{1-6}$alkyl;

X represents O, S, or $NR^{10}$, wherein $R^{10}$ represents hydrogen, $C_{1-6}$alkyl, or cyano;

$R^4$ represents Het, $Ar^2$, cyano, isocyanato, isothiocyanato, $Ar^2$-sulfonyl, or halo, wherein $Ar^2$ is as defined above;

$R^5$ represents hydrogen, Het, $Ar^2$, $C_{1-6}$alkyl, or $C_{1-6}$alkyl substituted with halo or $Ar^2$, wherein $Ar^2$ is as defined above; and $R^6$ represents hydrogen, Het, $Ar^2$, $C_{1-6}$alkyl, or $C_{1-6}$alkyl substituted with halo or $Ar^2$, wherein $Ar^2$ is as defined above; wherein Het represents:

(i) an optionally substitued five- or six-membered heterocyclic ring containinged 1, 2, 3, or 4 heteroatoms selected from the group consisting of oxygen, sulfur, and nitrogen, provided that no more than two oxygens or sulfurs are present; or (ii) an optionally substituted five- or six-membered heterocyclic ring containing 1 or 2 heteroatoms selected from the group consisting of oxygen, sulfur, and nitrogen, being fused with an optionally substituted five- or six-membered ring through two ring carbon atoms or one ring carbon and one ring nitrogen atom, containing in the remainder of the fused ring only carbon atoms; or (iii) an optionally substituted five- or six-membered heterocyclic ring containing 1 or 2 heteroatoms selected from the group consisting of oxygen, sulfur, and nitrogen, being fused with an optionally substituted five- or six-membered heterocyclic ring through two ring carbon atoms or one ring carbon and one ring nitrogen atom, containing in the remainder of the fused ring 1 or 2 heteroatoms selected from the group consisting of oxygen, sulfur and nitrogen; wherein:

Het may optionally be substituted with up to 4 substituents when Het is a monocyclic ring system, and wherein Het may optionally be substituted with up to 5 substituents when Het is a bicyclic ring system, said substitutents of Het being selected from the group consisting of a bivalent radical =X; halo; isocyanato; isothiocyanato; nitro; cyano; trifluoromethyl; a radical of formula —A; a radical of formula —Y—A; or a radical of formula —Z$^1$—C(=X)—Z$^2$—A; wherein =X is as defined above;

A represents hydrogen, Ar$^2$, or C$_{1-6}$alkyl being optionally substituted with Ar$^2$, C$_{1-6}$alkyloxy, Ar$^2$—O, hydroxy, or C$_{1-6}$alkyloxycarbonyl; and Y, Z$^1$, and Z$^2$ each have the meaning as defined above;

provided that (i) when in the radical —Z$^1$—C(=X)—Z$^2$—A, A is hydrogen and Z$^1$ is NR$^9$, O, or S, then Z$^2$ is other than O or S, and further provided that (ii) when L is C$_{1-2}$alkyl, R$^1$ is other than hydrogen, 2-methylphenyl, benzyl, 4-chlorobenzyl, or methoxybenzyl.

9. The compound of claim 8 wherein R$^4$, R$^5$, and R$^6$ represent Het.

10. The compound of claim 8 wherein:
R$^4$ represents Ar$^2$, cyano, isocyanato, isothiocyanato, Ar$^2$-sulfonyl, or halo;
R$^5$ represents hydrogen, Ar$^2$, C$_{1-6}$alkyl, or C$_{1-6}$alkyl substituted with halo or Ar$^2$; and
R$^6$ represents Ar$^2$, C$_{1-6}$alkyl, or C$_{1-6}$alkyl substituted with halo or Ar$^2$.

11. The compound of claim 8 wherein R$^1$ represents C$_{1-6}$alkyl substituted with Ar$^1$, or wherein R$^1$ represents —Alk—O—R$^2$ wherein R$^2$ represents hydrogen, C$_{1-6}$alkyl, C$_{2-6}$alkenyl, C$_{3-6}$alkynyl, or Ar$^1$.

12. The compound of claim 11 wherein R is hydrogen, m is 1, n is 1, and L is hydrogen, C$_{1-6}$alkyl, or a radical of formula (b-1), (b-2), or (b-3).

13. The compound of claim 12 wherein R$^4$ is Ar$^2$ or Het, R$^5$ and R$^6$ are C$_{1-4}$alkyl, X is O, S, and Z$^1$ and Z$^2$ are each independently NH or a direct bond.

14. The compound of claim 13 wherein R$^1$ is an ethoxyethyl group.

15. An anti-allergic composition comprising one or more pharmaceutical carriers and as active ingredient an anti-allergic effective amoung of at least one compound of the formula:

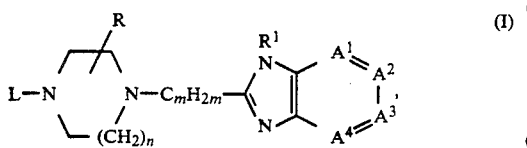
(I)

a pharmaceutically acceptable acid addition salt or a stereochemically isomeric form thereof, wherein:

—A$^1$=A$^2$—A$^3$=A$^4$— represents a bivalent radical of the formula:

—N=CH—N=CH—      (a-5) or;

—CH=N—CH=N—      (a-6), wherein one or two hydrogen atoms in said radicals (a-5) and (a-6) may, each independently from each other, be replaced by halo, C$_{1-6}$alkyl, C$_{1-6}$alkyloxy, trifluoromethyl, or hydroxy;

R represents hydrogen or C$_{1-6}$alkyl;

R$^1$ represents hydrogen, C$_{1-10}$alkyl, C$_{3-6}$cycloalkyl, Ar$^1$, C$_{1-6}$alkyl substituted with one or two Ar$^1$ radicals, or a radical of the formula —Alk—G—R$^2$, wherein:

Ar$^1$ represents phenyl; phenyl substituted with 1, 2, or 3 substituents each independently selected from halo, hydroxy, nitro, cyano, trifluoromethyl, C$_{1-6}$alkyl, C$_{1-6}$alkyloxy, C$_{1-6}$alkylthio, mercapto, amino, mono- and di(C$_{1-6}$alkyl)amino, carboxyl, C$_{1-6}$alkyloxycarbonyl, and C$_{1-6}$alkylcarbonyl; thienyl; halothienyl; furanyl; C$_{1-6}$alkyl substituted furanyl; pyridinyl; pyrimidinyl; pyrazinyl; thiazolyl; imidazolyl; or imidazolyl substituted with C$_{1-6}$alkyl;

Alk represents C$_{1-6}$alkanediyl;

G represents O, S, or NR$^3$, wherein R$^3$ represents hydrogen, C$_{1-6}$alkyl, C$_{1-6}$alkylcarbonyl, C$_{1-6}$alkyloxycarbonyl, or Ar$^2$—C$_{1-6}$alkyl;

Ar$^2$ represents phenyl or phenyl substituted with 1, 2, or 3 substituents each independently selected from halo, hydroxy, nitro, cyano, trifluoromethyl, C$_{1-6}$alkyl, C$_{1-6}$alkyloxy, C$_{1-6}$alkylthio, mercapto, amino, mono- and di(C$_{1-6}$alkyl)amino, carboxyl, C$_{1-6}$alkyloxycarbonyl, and C$_{1-6}$alkylcarbonyl; and R$^2$ represents hydrogen; C$_{2-6}$alkenyl; C$_{2-6}$alkenyl substituted with Ar$^2$; C$_{3-6}$alkynyl; Ar$^1$; C$_{1-6}$alkyl; or C$_{1-6}$alkyl substituted with Ar$^1$, hydroxy, C$_{1-6}$alkyloxy, carboxyl, C$_{1-6}$alkyloxycarbonyl, Ar$^2$-oxycarbonyl, or Ar$^2$—C$_{1-6}$alkyloxycarbonyl, wherein Ar$^1$ and Ar$^2$ are as defined above;

m represents a number having a value of from 1 to 4;
n represents a number having a value of from 1 to 2; and L represents hydrogen, C$_{1-6}$alkylcarbonyl, C$_{1-6}$alkylsulfonyl, C$_{1-6}$alkyloxycarbonyl, Ar$^2$—C$_{1-6}$alkyloxycarbonyl, Ar$^2$-carbonyl, Ar$^2$-sulfonyl, C$_{3-6}$cycloalkyl, C$_{2-6}$alkenyl, C$_{2-6}$alkenyl substituted with Ar$^2$, C$_{1-12}$alkyl, wherein Ar$^2$ is as defined above, or L represents a radical of the formula:

—Alk—R$^4$      (b-1);

—Alk—Y—R$^5$      (b-2); or

—Alk—Z$^1$—(C=X)—Z$^2$—R$^6$      (b-3)

wherein:
Alk is as defined above;
Y represents O, S, NR$^8$, wherein R$^8$ represents hydrogen, C$_{1-6}$alkyl, C$_{1-6}$alkylcarbonyl, or Ar$^1$-carbonyl, wherein Ar$^1$ is as defined above;
Z$^1$ and Z$^2$ each independently represent O, S, NR$^9$, or a direct bond, wherein R$^9$ represents hydrogen or C$_{1-6}$alkyl;
X represents O, S, or NR$^{10}$, wherein R$^{10}$ represents hydrogen, C$_{1-6}$alkyl, or cyano;

$R^4$ represents Het, $Ar^2$, cyano, isocyanato, isothiocyanato, $Ar^2$-sulfonyl, or halo, wherein $Ar^2$ is as defined above;

$R^5$ represents hydrogen, Het, $Ar^2$, $C_{1-6}$alkyl, or $C_{1-6}$alkyl substituted with halo or $Ar^2$, wherein $Ar^2$ is as defined above; and $R^6$ represents hydrogen, Het, $Ar^2$, $C_{1-6}$alkyl, or $C_{1-6}$alkyl substituted with halo or $Ar^2$, wherein $Ar^2$ is as defined above; wherein Het represents:

(i) an optionally substituted five- or six-membered heterocyclic ring containinged 1, 2, 3, or 4 heteroatoms selected from the group consisting of oxygen, sulfur, and nitrogen, provided that no more than two oxygens or sulfurs are present; or (ii) an optionally substituted five- or six-membered heterocyclic ring containing 1 or 2 heteroatoms selected from the group consisting of oxygen, sulfur, and nitrogen, being fused with an optionally substituted five- or six-membered ring through two ring carbon atoms or one ring carbon and one ring nitrogen atom, containing in the remainder of the fused ring only carbon atoms; or (iii) an optionally substituted five- or six-membered heterocyclic ring containing 1 or 2 heteroatoms selected from the group consisting of oxygen, sulfur, and nitrogen, being fused with an optionally substituted five- or six-membered heterocyclic ring through two ring carbon atoms or one ring carbon and one ring nitrogen atom, containing in the remainder of the fused ring 1 or 2 heteroatoms selected from the group consisting of oxygen, sulfur and nitrogen; wherein:

Het may optionally be substituted with up to 4 substituents when Het is a monocyclic ring system, and wherein Het may optionally be substituted with up to 5 substituents when Het is a bicyclic ring system, said substitutents of Het being selected from the group consisting of a bivalent radical =X; halo; isocyanato; isothiocyanato; nitro; cyano; trifluoromethyl; a radical of formula —A; a radical of formula —Y—A; or a radical of formula —$Z^1$—C(=X)—$Z^2$—A; wherein:

=X is as defined above;

A represents hydrogen, $Ar^2$, or $C_{1-6}$alkyl being optionally substituted with $Ar^2$, $C_{1-6}$alkyloxy, $Ar^2$—O, hydroxy, or $C_{1-6}$alkyloxycarbonyl; and Y, $Z^1$, and $Z^2$ each have the meaning as defined above;

provided that when in the radical —$Z^1$—C(=X)—$Z^2$—A, A hydrogen and $Z^1$ is $NR^9$, O, or S, then $Z^2$ is other than O or S.

16. The composition of claim 15 wherein $R^4$, $R^5$, and $R^6$ represent Het.

17. The composition of claim 15 wherein:

$R^4$ represents $Ar^2$, cyano, isocyanato, isothiocyanato, $Ar^2$-sulfonyl, or halo;

$R^5$ represents hydrogen, $Ar^2$, $C_{1-6}$alkyl, or $C_{1-6}$alkyl substituted with halo or $Ar^2$; and $R^6$ represents hydrogen, $Ar^2$, $C_{1-6}$alkyl, or $C_{1-6}$alkyl substituted with halo or $Ar^2$.

18. The composition of claim 15 wherein $R^1$ represents $C_{1-6}$alkyl substituted with $Ar^1$, or wherein $R^1$ represents —Alk—O—$R^2$ wherein $R^2$ represents hydrogen, $C_{1-6}$alkyl, $C_{2-6}$alkenyl, $C_{3-6}$alkynyl, or $Ar^1$.

19. The composition of claim 18 wherein R is hydrogen, m is 1, n is 1, and L is hydrogen, $C_{1-6}$alkyl, or a radical of formula (b-1), (b-2), or (b-3).

20. The composition of claim 19 wherein $R^4$ is $Ar^2$ or Het, $R^5$ and $R^6$ are $C_{1-4}$alkyl, X is O or S, and $Z^1$ and $Z^2$ are each independently NH or a direct bond.

21. The composition of claim 20 wherein $R^1$ is an ethoxyethyl group.

22. The method of claim 1 wherein the compound is a member selected from the group consisting of:

3-[2-[4-[[9-(2-ethoxyethyl)-9H-purin-8-yl]methyl]-1-piperazinyl]ethyl]-2-methyl-4H-pyrido[1,2-a]pyrimidin-4-one; and 6-[2-[4-[[9-(2-ethoxyethyl)-9H-purin-8-yl]methyl]-1-piperazinyl]ethyl]-7-methyl-5H-thiazolo[3,2-a]pyrimidin-5-one.

23. The compound of claim 8 wherein the compound is a member selected from the group consisting of:

3-[2-[4-[[9-(2-ethoxyethyl)-9H-purin-8-yl]methyl]-1-piperazinyl]ethyl]-2-methyl-4H-pyrido[1,2-a]pyrimidin-4-one; and 6-[2-[4-[[9-(2-ethoxyethyl)-9H-purin-8-yl]methyl]-1-piperazinyl]ethyl]-7-methyl-5H-thiazolo[3,2-a]pyrimidin-5-one.

24. The composition of claim 15 wherein the compound is a member selected from the group consisting of:

3-[2-[4-[[9-(2-ethoxyethyl)-9H-purin-8-yl]methyl]-1-piperazinyl]ethyl]-2-methyl-4H-pyrido[1,2-a]pyrimidin-4-one; and 6-[2-[4-[[9-(2-ethoxyethyl)-9H-purin-8-yl]methyl]-1-piperazinyl]ethyl]-7-methyl-5H-pyrido[3,2-a]pyrimidin-5-one.

* * * * *

UNITED STATES PATENT AND TRADEMARK OFFICE
CERTIFICATE OF CORRECTION

PATENT NO. : 5,086,056
DATED : Feb. 4, 1992
INVENTOR(S) : Frans E. Janssens, et al It is certified that error appears in the above-indentified patent and that said Letters Patent is hereby corrected as shown below:

Column 49 at line 7:

[X] should read "S"

Column 51 at line 51:

[X is O, S] should read "X is O or S"

Signed and Sealed this

Third Day of May, 1994

*Attest:*

BRUCE LEHMAN

*Attesting Officer*   Commissioner of Patents and Trademarks